United States Patent
Teicher

(10) Patent No.: US 9,791,539 B2
(45) Date of Patent: Oct. 17, 2017

(54) SYSTEM AND METHOD FOR MULTI-LEVEL BORDER CONTROL WITHIN SITES

(71) Applicant: TECHIP INTERNATIONAL LIMITED, Larnaca (CY)

(72) Inventor: Mordechai Teicher, Hod-Hasharon (IL)

(73) Assignee: TECHIP INTERNATIONAL LIMITED, Larnaca (CY)

( * ) Notice: Subject to any disclaimer, the term of this patent is extended or adjusted under 35 U.S.C. 154(b) by 0 days.

(21) Appl. No.: 15/211,232

(22) Filed: Jul. 15, 2016

(65) Prior Publication Data
US 2017/0069153 A1    Mar. 9, 2017

Related U.S. Application Data

(60) Provisional application No. 62/214,936, filed on Sep. 5, 2015.

(51) Int. Cl.
| | |
|---|---|
| A61B 5/11 | (2006.01) |
| G01S 5/02 | (2010.01) |
| G07C 9/00 | (2006.01) |
| G08B 21/02 | (2006.01) |
| G08B 21/22 | (2006.01) |
| G01S 1/68 | (2006.01) |
| G08B 13/24 | (2006.01) |
| G06K 17/00 | (2006.01) |

(52) U.S. Cl.
CPC ........... *G01S 5/0252* (2013.01); *A61B 5/1113* (2013.01); *G01S 1/68* (2013.01); *G07C 9/00111* (2013.01); *G07C 9/00126* (2013.01); *G08B 21/0261* (2013.01); *G08B 21/22* (2013.01); *G06K 2017/0045* (2013.01); *G08B 13/248* (2013.01); *G08B 13/2417* (2013.01); *G08B 21/0247* (2013.01); *G08B 21/0288* (2013.01)

(58) Field of Classification Search
CPC  G08B 21/0288; G08B 21/22; G08B 13/2417; G08B 13/248; G08B 21/0247; G08B 21/0261; G06K 2017/0045; A61B 5/1113
See application file for complete search history.

(56) References Cited

U.S. PATENT DOCUMENTS

| 7,821,391 B2 | 10/2010 | Gupta et al. |
| 9,240,084 B2 | 1/2016 | Vardi et al. |

(Continued)

*Primary Examiner* — Benyam Haile
(74) *Attorney, Agent, or Firm* — Nixon & Vanderhye P.C.

(57) ABSTRACT

A system and method for keeping restricted objects within a confined area that forms part of an institutional site. The confined area having lockable exits, a safe area where the restricted objects are designated to stay, a buffer area adjacent to the first area, and a lock area situated between the buffer area and the lockable exits. The system detects whether the restricted object is in the buffer area or in the lock area and checks whether the restricted object is authorized to leave the safe area. Upon recognizing that the restricted object is in the buffer area and is not authorized to leave the safe area, the system sends a message to a tag of a staff member, instructing to move the restricted object back to the safe area; upon recognizing that the restricted object is in the lock area and is not authorized to leave the safe area, the system sends a locking signal to lockable exits.

20 Claims, 20 Drawing Sheets

(56) References Cited

U.S. PATENT DOCUMENTS

| | | | |
|---|---|---|---|
| 9,240,119 B2 | 1/2016 | Vardi et al. | |
| 2005/0057359 A1 | 3/2005 | Coffey et al. | |
| 2006/0136997 A1 | 6/2006 | Telek et al. | |
| 2008/0007407 A1* | 1/2008 | de Elia | G08B 21/0261 340/572.1 |
| 2008/0088437 A1* | 4/2008 | Aninye | G07C 9/00111 340/539.13 |
| 2010/0039259 A1* | 2/2010 | Hazzani | G07C 9/00087 340/541 |
| 2010/0178913 A1 | 7/2010 | Herbert et al. | |
| 2010/0283600 A1 | 11/2010 | Herbert et al. | |
| 2012/0084467 A1 | 4/2012 | Birnbaum et al. | |
| 2012/0266071 A1 | 10/2012 | Chen | |
| 2014/0062695 A1* | 3/2014 | Rosen | G08B 21/18 340/539.13 |
| 2014/0297900 A1 | 10/2014 | Herbert et al. | |
| 2015/0194030 A1* | 7/2015 | Davidson | G08B 13/2468 340/572.7 |
| 2016/0148496 A1* | 5/2016 | Meredith | G08B 27/00 340/286.07 |

\* cited by examiner

SYSTEM AND METHOD FOR MULTI-LEVEL BORDER CONTROL WITHIN SITES

CROSS REFERENCE TO RELATED APPLICATIONS

This application claims the benefits of U.S. provisional patent application No. 62/214,936 filed on 5 Sep. 2015; this application is related to U.S. patent application Ser. No. 15/211,201 by the present inventor titled SYSTEM AND METHOD FOR LOCATING OBJECTS, filed concurrently with the present application (now U.S. Pat. No. 9,594,151 issued Mar. 14, 2017); the contents of both related applications are incorporated by reference in their entirety as if set forth herein.

BACKGROUND OF THE INVENTION

Field of the Invention

The present invention relates to locating objects, and in particular to locating assets and people within institutional sites.

Description of Related Art

RTLS (real time location services) systems are commonly used to locate objects, such as assets or people, within institutional sites such as manufacturing plants, warehouses, healthcare facilities or retail stores.

A typical RTLS system includes an infrastructure of fixed active devices, each located at a known location, and movable active devices, each associated with a known object. The fixed and movable active devices are adapted to establish short-range communication via an ultrasonic, infrared or low-power RF signal, and at least one of the fixed or movable active devices connects via a network to report meetings between respective active devices. Each meeting report indicates that the current location of the object associated with the movable active device is in proximity to the known location of the fixed active device, thereby providing real time location information related to the respective object.

The resolution of the detected location can be improved in a variety of ways, such as: a shorter communication range and higher number of fixed active devices; analyzing the signal strength, sometimes is association with the battery level, for estimating the current distance between the reported devices; or using triangulation for analyzing a plurality of simultaneous short-range signals associated with a single movable active device and a plurality of fixed active devices.

A typical RTLS system requires substantial investment in sensing and communication infrastructures throughout the site. While some sites justify such investment by effectively and quickly locating critical equipment or personnel, and others show high returns from targeted advertising, there are still many other sites that could benefit from quickly locating objects, and cannot afford or justify the expense associated with deploying the respective sensing and communication infrastructure of a common RTLS system.

The present disclosure comes to teach locating systems with highly reduced sensing and communication infrastructures, and some applications of such systems.

BRIEF SUMMARY OF THE INVENTION

Definitions

An "institutional site", abbreviated "site", is a managed place that is run by a "staff". Examples of sites include manufacturing plants, warehouses, healthcare facilities or retail stores. A "staff member" is an employee or volunteer operating in a site. A "mover" is a staff member designated to move an asset to a specified target location. Being a mover may be the main job of a staff member, or an occasional incident. A site may accommodate additional persons that are not staff members, such as residents, customers or visitors.

An "asset" is a thing that may be needed for a useful purpose. People are not considered herein assets, and the term "object" will be used herein to refer to both people and assets that need to be located. An "asset identifier", such as an inventory number, uniquely identifies an asset within a site. An asset identifier may also include a human-comprehensible "asset description" to describe an asset to staff members; examples for asset descriptions are the respiratory machine, respiratory machine no. 37, or the yellow respiratory machine.

An "active device" is an electronic devices capable of transmitting and/or receiving data.

A "smart tag", abbreviated "tag", is herein an active device that plays a role in locating objects and is capable of communicating location information. Smart tags include "personal tags" borne by persons, "asset tags" attached to assets, and "fixed tags" that are fixed at a location. In a healthcare facility, personal tags include "staff tags" and "resident tags" borne by staff members and residents, respectively, or may further include "visitor tags" borne by visitors. A tag is preferably configured according to the respective role and identity of the person, asset or location associated with the tag. A personal tag may be a dedicated device assigned to a person, or a private communication device of a person, such as a smartphone, programmed to function as a tag.

A "beacon" is an active device recurrently transmitting a short-range signal for being received and read by tags that are within a short maximum range, the preferred maximum range being between a meter and a few tens of meters, depending on the application. A "location beacon" is fixed to a specific location within a site, such as on a wall or a ceiling; an "asset beacon" is attached to an asset and moves with the asset; while a "personal beacon" is borne by and moves with a person. The term "attached to an asset" covers also the case where the beacon forms an integral part of the asset. As long as a certain object beacon is known to be borne by or attached to a certain object, expressions such as "detecting an object", "detecting an object beacon"; "locating an object", "locating an object beacon"; "receiving a signal from an object", or "receiving a signal from an object beacon"; may be used interchangeably. The short-range signal transmitted by the beacon preferably uses low-power RF, ultrasound or infrared to carry the "beacon identifier" uniquely identifying the beacon within the site, and possibly also information regarding the battery level of the beacon, and/or object status information received by the beacon from an object by which the beacon is borne or to which the beacon is attached. A beacon short-range signal is read by a compatible receiver that forms part of a tag or another signal detecting device, to identify the beacon and possibly also identify the object by whom the beacon is borne to which the beacon is attached, as well as to optionally receive other information carried by the signal. A receiver may also measure the strength of the short-range signal received from a beacon, which may be indicative of the current distance between the receiver and the beacon, which is similar to the distance between the tag and the object. iBeacon, marketed by numerous vendors in compliance with a standard published by Apple, Cupertino, Calif., is an example of a beacon that uses BLE (Bluetooth low energy) for its short-range signal, while a variety of contemporary smartphones can be programmed to act as compatible receivers.

A "visual feature" is a distinguishable visual mark, symbol, pattern, image or color that can be captured by a camera and processed by an image processor to identify a location, an object or an object type. Visual features may be invisible to the naked eye, for example by using ink in the infrared wavelength, as long as the respective cameras can see them and use appropriate filters, if needed. In the present context, visual features may be borne by objects or fixed to locations, and function similarly to beacons, if respective tags have cameras and are adapted to detect and recognize them.

"Bearing" a tag, a beacon or a visual feature by an object will generally relate to a person carrying or wearing a tag, a beacon or a visual feature, or an asset having a tag, a beacon or a visual feature attached thereto or embedded therein.

It shall be appreciated that some active devices may function as both tags and beacons. Thus, a tag may locate another tag via short-range communication.

Databases that are stored in or are accessible by tags may correlate object identifiers with beacon identifiers and object descriptions, and it is presumed herein that providing an object identifier to a tag makes the corresponding beacon identifiers and/or asset descriptions readily available to the tag.

"Locating" an object means obtaining information pertaining to the current location of the object, while "directing" toward an object means providing human-comprehensible directions to a person for reaching the object according to its location.

SUMMARY

The following discussion mostly uses examples pertaining to healthcare facilities. However, it shall be appreciated that the teachings of the present disclosure relate to a variety of other institutional sites as well.

The present disclosure recognizes that, under certain circumstances, a locating and directing system can be highly simplified by realizing, and making use of the fact, that assets are usually moved by staff members; that staff members are often intelligent, experienced persons who are familiar with the assets and the site and typical locations where assets are used or parked, and have eyes; and that staff members often accidentally pass by assets in the course of performing their routine duties.

The following concepts will facilitate the understanding of the present disclosure:

"Zoning" is a division of a site into relatively large zones, serving for roughly locating objects. The term zoning will also be used herein to denote the act of zone-level locating of an object, i.e. identifying the zone in which an object resides. It is assumed that, under certain circumstances, zoning may be good enough for effective, timely locating of objects; for example, a staff member requested to "fetch a respiratory machine from the West Zone on the $3^{rd}$ floor" will often reach the machine pretty quickly, may be just a few seconds later than when being requested, in another similar site employing a common, fully-fledged RTLS system, to "fetch a respiratory machine from next to bed C in room 305". Zones may partly overlap, thus zoning may afford some level of ambiguity, as will be elaborated later below.

"Homing" is a method for directing a user holding a receiver toward a target asset having an asset beacon, by seeking a short-range signal transmitted by the target asset, and when the short-range signal is detected, continuously monitoring the short-range signal for approaching the asset, for example by exhibiting a series of human-comprehensible homing directions toward the asset, based on the receiver providing to the user a series of visual and/or audio indications of the current measured strength of the signal received from the beacon, that may be presented in terms of estimated distance, which intuitively leads the user to seek stronger signals hence approach the asset. In more sophisticated systems, homing may provide explicit direction indications, such as by displaying an arrow pointing at the asset. Homing may complement zoning for fast screening of larger zones, including, for example: for finding the asset faster; for distinguishing a sought specific asset from other similar assets; for finding assets that hide behind curtains that are permeable to the beacon's short-range signal; for indicating, by an absence of a beacon signal, that the sought asset is not within a certain part of the zone; or just for verifying that the related asset is in the zone without physically approaching the asset.

"Greeting" is an asset location report message authored and sent by a tag that has detected the beacon of the asset, thereby associating the location of the asset with the zone of the tag. A greeting may be informally described as a message sent by a tag to a recipient, stating: I am currently in zone X and have just seen asset Y. In a typical healthcare facility, for example, many tags are continually passing by assets, purposely or accidentally, providing a continuous series of greetings that serve to dynamically locate assets, as will be further elaborated below.

"Escorting" is an event of detecting continuous close proximity between a tag and an asset beacon maintained for a prolonged duration, say thirty seconds or more, while also detecting that the tag has moved a substantial distance, say several meters or more, during the duration of the close proximity. An escorting event may be interpreted as a displacement of the respective asset by the person bearing the tag. If a staff member has been commissioned to move a certain asset to bed C in room 305, then the respective escorting event may indicate by default that at the end of the escorting event the asset is located next to bed C in room 305.

According to preferred embodiments of the present invention, there is thus provided a system for keeping a restricted object within a confined area that forms part of an institutional site, the confined area having: (i) one or more lockable exits, (ii) a first area, that is a safe area where the restricted object is designated to stay, (iii) a second area, that is a buffer area adjacent to the first area, and (iv) a third area, that is a lock area situated between the buffer area and the one or more lockable exits. The system includes: a first detector, detecting whether the restricted object is in the second area; a second detector, detecting whether the restricted object is in the third area; and at least one processor programmed to:
  communicate with the first detector and the second detector to identify whether the restricted object is in the second area or in the third area,
  check whether the restricted object is authorized to leave the first area,
  upon recognizing that the restricted object is in the second area and is not authorized to leave the first area: send a message to a tag of at least one staff member, the message instructing to move the restricted object back to the safe area, and upon recognizing that the restricted object is in the third area and is not authorized to leave the first area: send a locking signal to at least one lockable exit of the one or more lockable exits.

It will be noted that each of the first and second detectors may include one or more location detection units, such as: tags attached to restricted objects communicating with fixed beacons located within the second and thirds areas or located at or next to the border between areas; or fixed tags located within the second and third areas or located at or next to the border between areas and communicating with beacons attached to restricted objects. The processor(s) may include processors of tags and/or of control units that communicate with tags.

The system may further employ its processor(s) to detect one or more staff members that are currently in vicinity of the restricted object, and select the at least one staff member from the one or more staff members that are currently in vicinity of the restricted object. The system may further operate to wait for acknowledgement from a tag of a staff member of the at least one staff member, and if no acknowledgement is received within a predefined period of time: send a message to a tag of at least one additional staff member.

The restricted object may be, for example, a restricted resident of a healthcare facility, or a restricted asset. The check whether the restricted object is authorized to leave the first area may be made, for example, by verifying that the restricted object is accompanied by a person authorized to move the restricted object.

Also provided is a system for keeping a restricted object within a confined area that forms part of an institutional site, the confined area having: (i) one or more lockable exits, (ii) a first area, that is a safe area where the restricted object is designated to stay, (iii) a second area, that is a buffer area adjacent to the first area, and (iv) a third area, that is a lock area situated between the buffer area and the one or more lockable exits, the system including:
 an object identifier, that is a beacon or a visual feature, borne by the restricted object;
 a first fixed tag operative to: communicate with the object identifier to detect whether the restricted object is in the second area, check whether the restricted object is authorized to leave the first area, and upon recognizing that the restricted object is in the second area and is not authorized to leave the first area: send a message to a tag of at least one staff member, the message instructing to move the restricted object back to the safe area; and
 a second fixed tag operative to: communicate with the object identifier to detect whether the restricted object is in the third area, check whether the restricted object is authorized to leave the first area, and upon recognizing that the restricted object is in the third area and is not authorized to leave the first area: send a locking signal to at least one lockable exit of the one or more lockable exits.

It will be noted that while the object identifier and the first and second fixed tags are described in singular language for simplicity and brevity, each of the elements represents one or more similar units that operate individually and/or cooperatively (e.g. by using triangulation) for detecting whether restricted objects are within the second or third areas.

Also provided is a system for keeping a restricted object within a confined area that forms part of an institutional site, the confined area having: (i) one or more lockable exits, (ii) a first area, that is a safe area where the restricted object is designated to stay, (iii) a second area, that is a buffer area adjacent to the first area, and (iv) a third area, that is a lock area situated between the buffer area and the one or more lockable exits, the system including:
 a first beacon fixed at the border of or within the second area;
 a second beacon fixed at the border of or within the third area; and
 a tag attached to the restricted object and selectively operating to communicate with the first beacon to detect whether the restricted object is in the second area, communicate with the second beacon to detect whether the restricted object is in the third area, check whether the restricted object is authorized to leave the first area, and: (i) upon recognizing that the restricted object is in the second area and is not authorized to leave the first area: send a message to a tag of at least one staff member, the message instructing to move the restricted object back to the safe area, and (ii) upon recognizing that the restricted object is in the third area and is not authorized to leave the first area: send a locking signal to at least one lockable exit of the one or more lockable exits.

It will be noted that while the tag and the first and second beacons are described in singular language for simplicity and brevity, each of the elements represents one or more similar units that operate individually and/or cooperatively (e.g. by using triangulation) for detecting whether restricted objects are within the second or third areas.

There is further provided a method of operation of at least one processor for keeping a restricted object within a confined area that forms part of an institutional site, the confined area having one or more lockable exits, the method including:
 recognizing, within the confined area: (i) a first area, that is a safe area where the restricted object is designated to stay, (ii) a second area, that is a buffer area adjacent to the first area, and (iii) a third area, that is a lock area situated between the buffer area and the one or more lockable exit;
 detecting whether the restricted object is in the second area or in the third area;
 checking whether the restricted object is authorized to leave the first area;
 upon recognizing that the restricted object is in the second area and is not authorized to leave the first area: sending a message to a tag of at least one staff member, the message instructing to move the restricted object back to the safe area; and
 upon recognizing that the restricted object is in the third area and is not authorized to leave the first area: sending a locking signal to at least one lockable exit of the one or more lockable exits.

The method may further include, prior to sending the message to the tag of at least one staff member: selecting the at least one staff member from one or more staff members that are currently in vicinity of the restricted object. Further, the method may include: waiting for acknowledgement from a staff member of the at least one staff member; and if no acknowledgement is received within a predefined period of time: sending a message to a tag of at least one additional staff member. The restricted object may be, for example, a restricted resident of a healthcare facility, or a restricted asset. Checking whether the restricted object is authorized to leave the first area may be made, for example, by verifying that the restricted object is accompanied by a person authorized to move the restricted object.

It will be noted that when locating objects is described as based on analyzing short-range communication between a fixed active device and a moving active device, additional fixed active devices may concurrently communicate with the same moving active device, for increasing location measurement resolution and accuracy, for example by triangulation. Such locating techniques are well-known in the art, and may be selectively implemented in the appropriate cases, even if they are not explicitly described.

BRIEF DESCRIPTION OF SEVERAL VIEWS OF THE DRAWINGS

The present invention will be understood and appreciated more fully from the following detailed description, taken in conjunction with the drawings in which.

DETAILED DESCRIPTION OF PREFERRED EMBODIMENTS OF THE INVENTION

The System

Figure 1A:
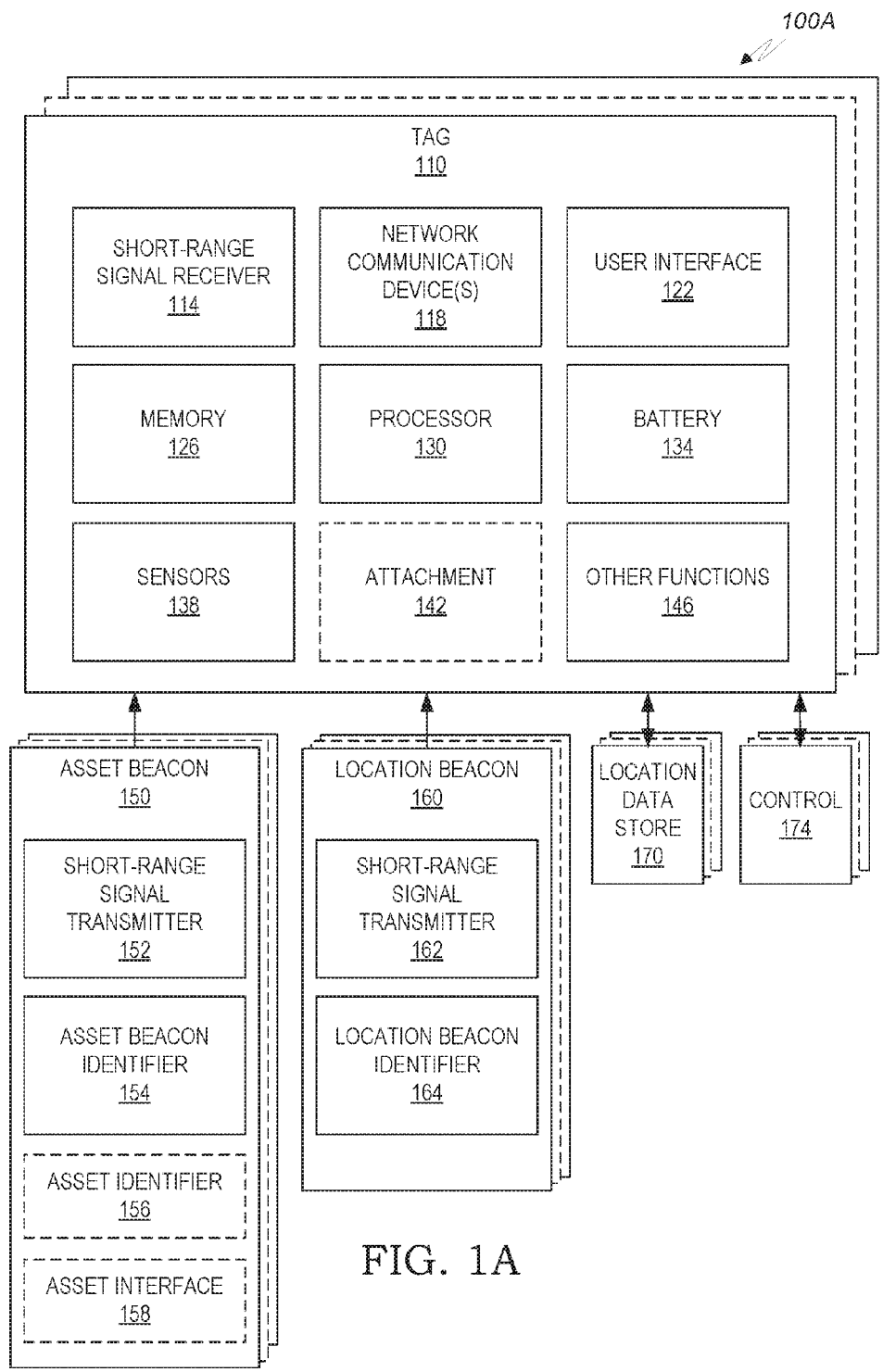
FIGS. 1A-1B are block diagrams describing systems according to preferred embodiments of the present invention.

FIG. 1A is a block diagram depicting system 100A according to a preferred embodiment. Each tag 110 of plurality of tags listens to short-range signals that may be transmitted by each asset beacon 150 of a plurality of asset beacons. Tag 110 also listens to short-range signals that may be transmitted by each asset location beacon 160 of a plurality of asset location beacons. Tag 110 sends location reports to one or more recipients having a location data store 170, and, if tag 110 is of a staff member that may be assigned to approach assets, tag 110 may also communicate with one or more control 174 for receiving asset-related assignments therefrom.

Tag 110 includes short-range signal receiver 114 that listens to signals sent by beacons and detects, from signals received from a beacon, the beacon identifier, and may also measure the strength of received signals. Optionally, short-range signal receiver 114 also retrieves from a signal received from a beacon other information, such as a message from an asset relayed via the respective asset beacon. One or more of network communication device(s) 118, is used for establishing communication via a communication network, such as a Wi-Fi, cellular or Bluetooth network, with location data store 170, and optionally also with control 174. User interface 122 provides information to the tag's user via visual and/or audio and/or tactile signals. Memory 126 stores data, while processor 130 includes processing hardware and software for the operation of tag 110, including the methods taught by the present disclosure. Battery 134 energizes all the units of tag 110. Sensors 138, such as an accelerometer, compass, microphone or camera, may be used to detect whether tag 110 is in use or is in motion, and also optionally participate in determining the location of tag 110. Optional other functions 146 are hardware and software components that serve for the tag offering useful functionalities that are unrelated to the present invention, such as music playing, telephony or outdoors navigation. Optional attachment 142, such as a lanyard, a belt or a clip, may be used to conveniently attach tag 110A the tag bearer's body or clothing. Tag 110A may also be carried in the bearer's handbag or pocket, for example in the case that the tag is actually implemented as a personal smartphone programmed according to the teachings of the present disclosure.

Asset beacon 150 is a transmitter of a short-range signal, such as an ultrasonic, infrared or low-power RF signal, that is assigned and attached to an asset and effectively becomes part of the asset. It is energized from either a battery (not shown) or from power provided by the asset. Asset beacon 150 is devised to recurrently transmit a short-range signal, for allowing receivers, such as short-range signal receiver 114 of tag 110, to detect the presence and retrieve the identity of the respective asset. Short-range signal transmitter 152 transmits the above short-range signal carrying asset beacon identifier 154 and/or asset identifier 156 and optionally messages received from the respective asset via asset interface 158. Asset beacon identifier 154 is recorded within asset beacon 150 to uniquely identify asset beacon 150 within the site. Asset identifier 156, such as an inventory number and/or an asset description, is optionally recorded within asset beacon 150, or it can be retrieved from a lookup table (not shown) included in the tag's memory 126 or in location data store 170, against asset beacon identifier 154. Asset interface 158 is optionally included, typically for more sophisticated and expensive assets, for relaying, via short-range signal transmitter 152, asset-related status messages such as usage, need for maintenance etc., and can also be used for supplying power from the asset for the operation of asset beacon 150.

Location beacon 160 is fixed at a known, selected spot, such as on a wall or a ceiling within the site, for identifying the current zone of a tag 110 that currently communicates with location beacon 160 via short-range communication. Location beacon 160 uses short-range signal transmitter 162 to transmit its location beacon identifier 164, which, when received by short-range signal receiver 114 of a tag 110, identifies the current zone in which tag 110 is currently located. The transformation from location beacon identifier 164 to the current zone is made by either processor 130 of tag 110 or at the location data store 170, using a site map that correlates each location beacon identifier 164 with its actual location within the site. Location beacon 160 can be classified into zone-border beacon or zone-center beacon, as will be elaborated later below.

Location data store 170 receives location data reports, also called herein greetings, from tags 110, and stores the received data for being used by control 174. The location data is preferably organized as a database or another data structure, and correlates asset beacon identifiers and/or asset identifiers with the current known location of each asset. Location data store 170 may be stored on a site server or internet server, on a desktop, laptop or tablet computer or a smartphone, or within memory 126 of tag 110 assigned to a staff member who is in charge of asset management or operates control 174. Several units of location data store 170 may operate concurrently, for example to serve different types of assets controlled by different controls 174, or just carry redundant copies of the same asset location data.

Control 174 is a computerized command post, that includes a processor, and is in a form such as a computer, a tablet, a smartphone or a staff tag, allowing a supervisory staff member, such as an asset manager, shift supervisor or chief nurse, to assign asset-related assignments to other staff members via their tag 110. When an asset-related assignment, such as maintaining or moving the asset, or authorization to move an asset, is assigned to a staff member bearing a tag 110, the tag will direct the staff member toward the asset, as will be described later below.

Figure 1B:
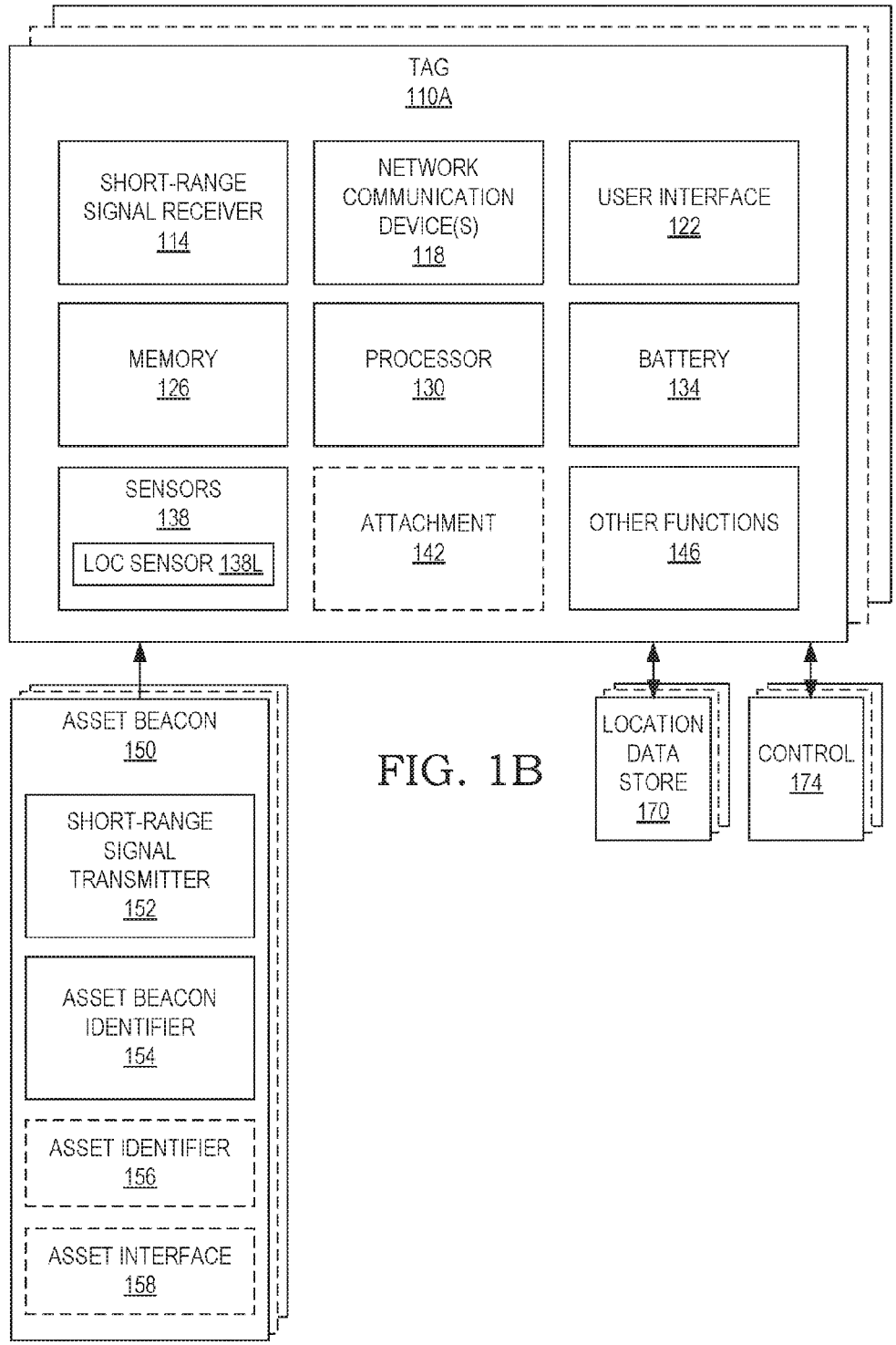

FIG. 1B describes system 100B, that is an alternative embodiment that does not use the location beacons 160 of FIG. 1A. Instead, one or more of location sensor 138L serve to identify the current zone where tag 110A is. Examples of location sensor 138L will be described in the section LOCATING TAGS WITHOUT USING LOCATION BEACONS below. It will be appreciated that hybrid configurations, that mix both location beacons 160 of FIG. 1A and one or more methods that do not use location beacons are also feasible, and may be the preferred choice for some sites.

Zoning

Zoning a site into relatively large zones serves for roughly defining a location of an object. Such division is site-specific, and may be made manually by an administrator under the following considerations: (a) easy recognition of the zone by staff members, for example: "the West Zone on the $3^{rd}$ floor" or "the imaging division"; (b) efficient and convenient deployment of location beacons or visual features used for identifying the zones (FIGS. 2B and 2C below), if such elements are applied; (c) the zone size and layout are easy to manually screen by a moving staff member for finding an asset within the zone; and (d) preferably, effective separation among zones, for example by walls that are impermeable to beacon signals, so that leaks of asset beacon signals between zones are eliminated or reduced.

Figure 2A:
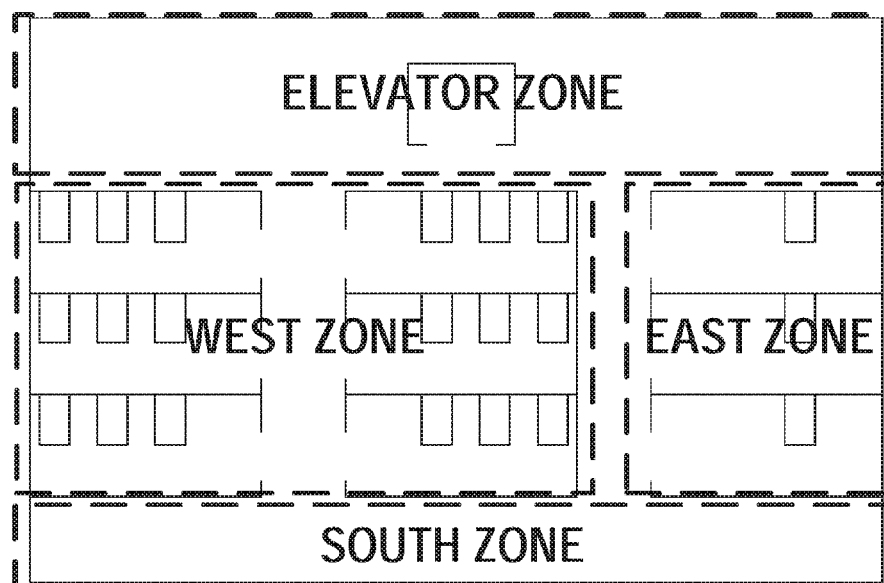
FIGS. 2A-2F are schematic illustrations of floor layouts of preferred embodiments of the present invention.

FIG. 2A schematically describes an exemplary division of a floor layout in a healthcare facility into four zones: Elevator Zone near the elevator; West Zone that includes six 3-bed rooms; East Zone that includes three single-bed rooms, and South Zone that is a corridor connecting the east and West Zones. It will be noted that zone names may be arbitrarily chosen by an administrator to be uniquely and easily recognized by the staff, and can be names of divisions, functional names such as the dining area, or legacy names such as "Roberta's hall".

Locating an Asset

Locating an asset is at least determining the zone in which the asset is currently located. In some cases, when additional information is available, as is the case of detecting an escorting event by a designated mover, such additional information may provide more specific location information; for example, instead of just locating a respiratory machine at the West Zone, it may be located next to bed C in room 305, according to the particulars of the moving assignment sent to the designated mover.

Locating an asset is usually a two-stage process: (i) locating a tag; and (ii) detecting the asset's beacon by the tag via a short-range signal. This locating process works best when the maximum range of the short-range signal is small relatively to the zone's size, and/or when zones are physically separated by walls that are impermeable to or highly attenuate the short-range signals. As noted above, the locating process may be supplemented by additional location information, as in the case of an escorting event by a designated mover.

It will be noted that locating the tag and detecting the asset's beacon may be separate events. For example, a staff member's tag detects its entry into the West Zone at 10:00 am, while the tag detects an asset beacon at 10:03 am. Such events are usually combined and interpreted as the respective asset being located at the West Zone at 10:03, especially when the tag is expected to reliably detect its exit from the West Zone.

Using Zone Border Beacons for Locating Tags

A "zone border beacon" is herein a location beacon positioned on or next to a border between zones, for allowing tags to detect their entering and/or exiting the respective zones. In some of the following exemplary embodiments such location beacons will be described as fixed to the ceiling; it will be appreciated, however, that location beacons may alternatively be fixed to walls or to any stationary objects.

Figure 2B:
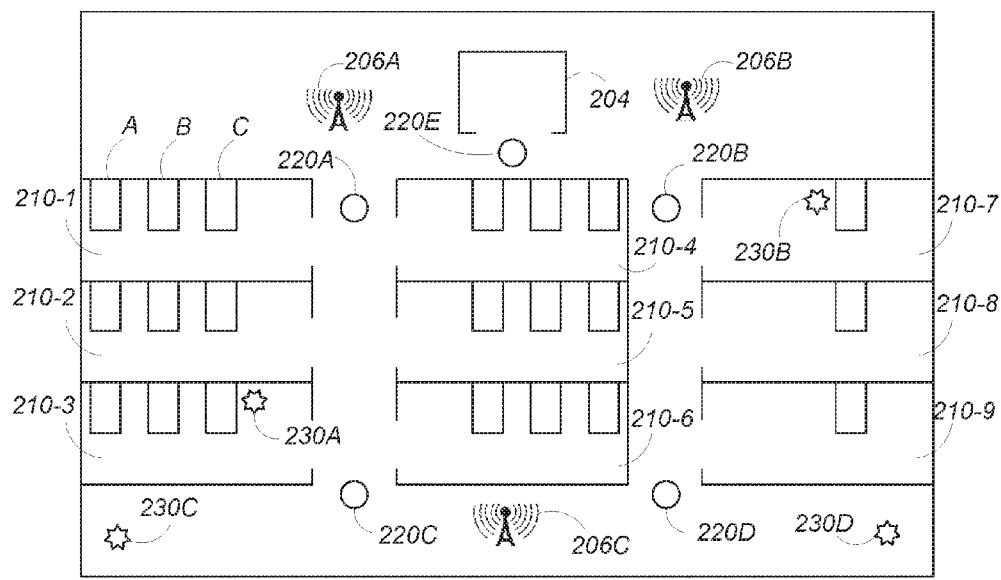

FIG. 2B schematically describes deployment of five zone border beacons 220A-220E, devised for allowing tags to detect entry into and exit from the four zones of FIG. 2A. The zone border beacon is preferably fixed to the ceiling or to a lintel, or possibly to a wall, on or next to the border between the zones. Thus, zone border beacon 220E is positioned for allowing tags to detect entry to and exit from the elevator into and from Elevator Zone; zone border beacon 220A and zone border beacon 220B are positioned for tags detecting moving between the Elevator Zone and the West Zone/East Zone, respectively; while zone border beacon 220C and zone border beacon 220D are positioned for tags detecting moving between the South Zone and the West Zone/East Zone, respectively.

Detection by a tag of crossing the border between zones benefits from the short distance and clear line-of-sight between the tag and the zone border beacon, and by recognizing a peak in the strength of the signal received by the tag from the beacon.

Figure 3:
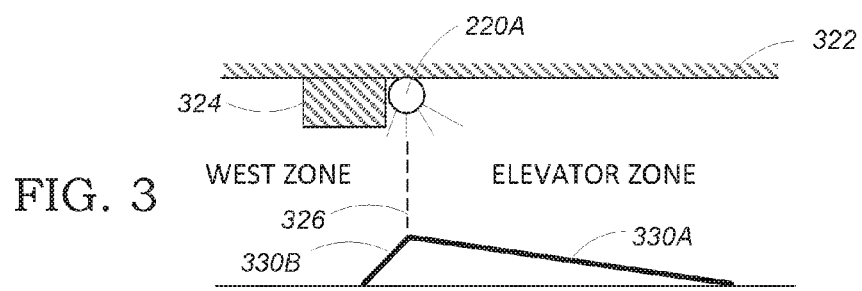
FIG. 3 is a schematic illustration depicting asymmetry purposely included in a zone border beacon according to a preferred embodiment of the present invention.

Deciding whether a border-crossing tag is entering or exiting a zone can be made by counting the number of crossings of the border by the tag. However, to avoid confusion, such as when a tag bearer turns around at the border between zones, asymmetry in the zone border beacon design or in its installation is preferably introduced. FIG. 3 schematically describes a simplified asymmetric design, where zone border beacon 220A is fixed to ceiling 322, and shield 324, such as a small piece of material that is impermeable to the short-range signal emitted from zone border beacon 220A, is also fixed to ceiling 322 to partially block the short-range signals emitted from zone border beacon 220A in the direction of the West Zone. The beacon signal strength detected by the tag is schematically depicted by curves 330A+330B as a function of distance from zone border 326 (straight curves are arbitrarily used for simplicity). Assuming that the tag moves with its bearer at a fairly constant speed, the signal vs. time curve looks similar to the signal vs. distance curve of FIG. 3. Thus, when the tag first detects moderate inclining slope signal strength curve 330A followed by sharp declining slope signal strength curve 330B, entry into the West Zone is detected, while when the tag first detects inclining sharp slope signal strength curve 330B followed by declining moderate slope signal strength curve 330A, entry into the Elevator Zone is detected. It will be noted that other designs that indicate the direction of motion between zones may be applied, for example placing a pair of beacons at the border between zones, and detecting which of the two respective peaks shows first.

Exemplary Floor Layout

FIG. 2B depicts an exemplary floor layout 200B in a healthcare facility, divided into the four zones of FIG. 2A. Elevator 204 is used to enter and exit the floor. The West Zone includes six rooms 210-1 to 210-6, each room hosting three beds A-C. The East Zone includes tree single-bed rooms 210-7 to 210-9. Zone border beacons 220A-220E serve tags visiting the floor (not shown) for locating their current zones by detecting border crosses, as discussed above. Assets 230A-230D are examples of assets scattered throughout the floor, to be located according to the teachings of the present disclosure. Access points 206A-206C, such as Wi-Fi access points, demonstrate partial network coverage of the floor, which allows a tag 110 to use its network communication device 118 (see FIGS. 1A-1B) to report asset locating events only passing by an access point.

Locating Tags without Using Location Beacons

Figure 2C:
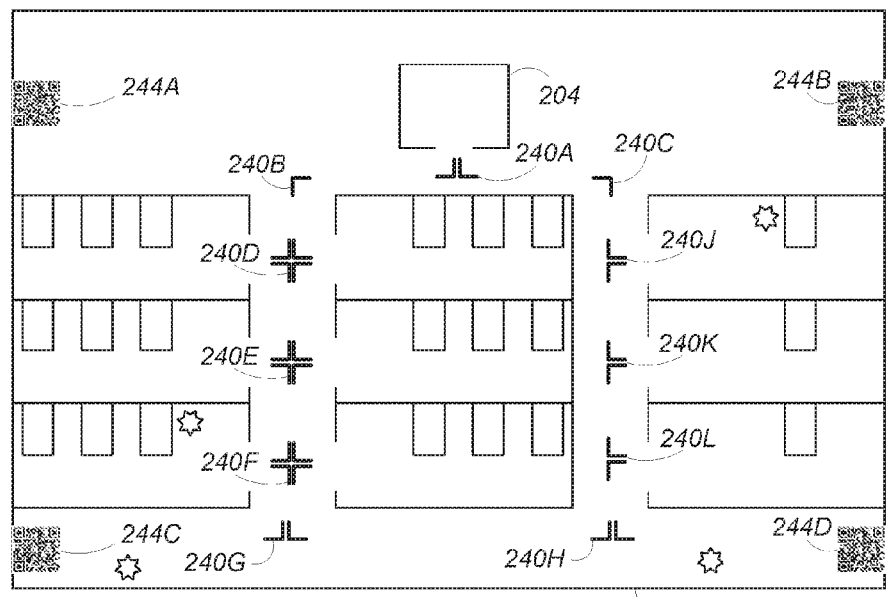

FIG. 2C describes floor layout 200C that is similar to floor layout 200B of FIG. 2B, with the omission of zone border beacons 220A-220E and with the addition of visual features 244A-244D. Retaining the method of locating an asset via combining locating a tag and detecting the asset's beacon by the tag, FIG. 2C focuses on using one or more of location sensor 138L (FIG. 1B) as alternatives to detecting the zone border beacons of FIG. 2B. Turning opportunities 240A-240L are virtual spots where tags may make sharp turns into or from corridors and rooms. Such turns are detectable by an accelerometer included in sensors 138, and may sometimes be distinguishable from one another with the assistance of a compass included in sensors 138.

With reference also to the zones defined in FIG. 1A, a tag detecting a sharp right turn at the elevator exit (apparently at turning opportunity 240A) followed by detecting a sharp left turn (apparently at turning opportunity 240B) may realize that the tag has entered the West Zone. However, when a further sharp right turn event is detected, it may be hard to determine whether such event occurred in any of turning opportunities 240D-240F—which implies that the tag is located in one of the rooms of the West Zone, or at turning opportunity 240G—implying that the tag has crossed the border to the South Zone. To resolve such ambiguities, visual features 244A-244D are added, to be detected and recognized by a camera that is included in sensors 138 and is positioned, along with the tag, to look at the same direction as the user bearing the tag. Thus, following the detection of the sharp right turn described above, seeing or missing visual feature 244C by the camera may indicate being at the South or West Zone, respectively. Visual features 244A-244D are distinctive marks, symbols, patterns, images or colors that are recognized by image processing of the image viewed by the camera, and can be, for example, either arbitrary existing elements, such as a painting hung on the wall, or a sticker or sign showing conventional text of coded with a bar code or QR code. A combination of analyzing all turning opportunities within a floor supplemented by unique visual features positioned at key points may provide reliable locating for tags within the floor area, as an alternative to location beacons.

Additionally or alternatively, other indoors positioning technologies may also be used for locating a tag. For example, U.S. Pat. No. 8,798,924 teaches a method of using an electronic compass sensor to detect consistent irregularities in the earth's magnetic field caused by steel structures embedded within buildings. The method has been implemented and marketed by IndoorAtlas Inc. of Palo Alto, Calif. Thus, including an electronic compass in sensors 138 of tag 110 and programming the method of the '924 patent above into processor 130 provides another way for locating the current zone of tag 110 without deploying location beacons.

Locating Tags Using Zone Center Beacons

A "zone center beacon" is a location beacon positioned within a zone, with the purpose of tags locating themselves within the zone upon detecting a short-range signal received from the zone center beacon, or upon detecting that the strength of the signal exceeds a predetermined threshold. It will be appreciated that the term "center" is merely illustrative, and a zone center beacon may be located anywhere within a zone, as long as detecting the beacon indicates being located within the respective zone. Also, a zone may have multiple zone center beacons (not shown in the following figures) that serve to identify the zone. In some of the following exemplary embodiments such location beacons will be described as fixed to the ceiling; it will be appreciated, however, that location beacons may alternatively be fixed to walls or to any stationary objects.

Figure 2D:
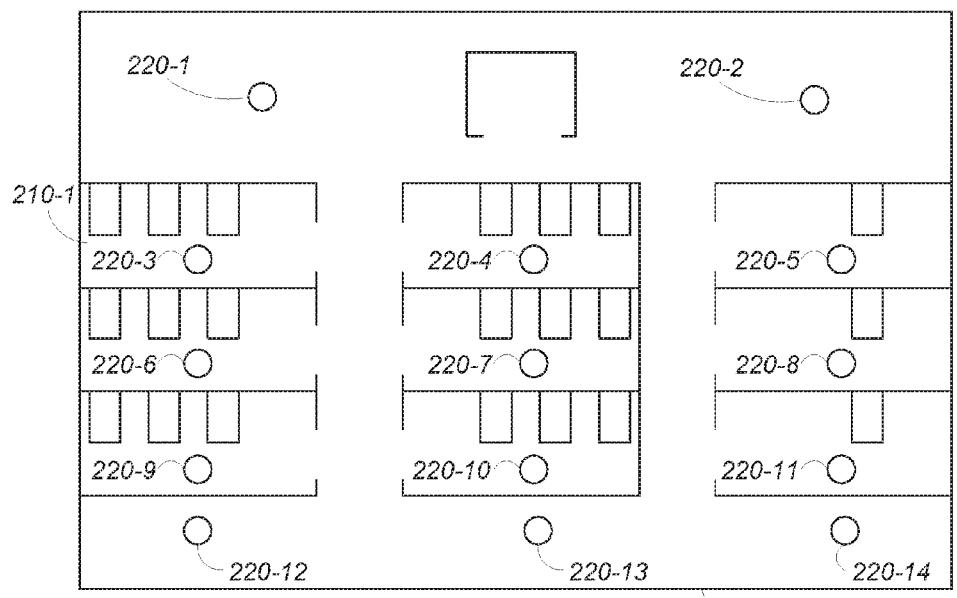

FIG. 2D schematically describes floor layout 200D, wherein fourteen zone center beacons 220-1 to 220-14 are fixed to the ceiling to define fourteen room-size zones. For example, when a tag detects zone center beacon 220-3 (or that the strength of the short-range signal received from zone center beacon 220-3 exceeds a predefined threshold), the tag is considered located within the respective room 210-1.

When comparing the exemplary layouts of FIGS. 2B and 2C, floor layout 200D appear to offer an advantage of finer, room-level locating resolution against the disadvantage of higher cost of deploying and maintaining more location beacons. However, smaller zones imply also other disadvantages of false locating and reduced frequency of greetings, as will be elaborated in the section CORRELATION BETWEEN ZONE SIZES AND ASSET BEACON SIGNAL RANGES below.

Dividing a Large Hall into Overlapping Zones

Figure 2E:
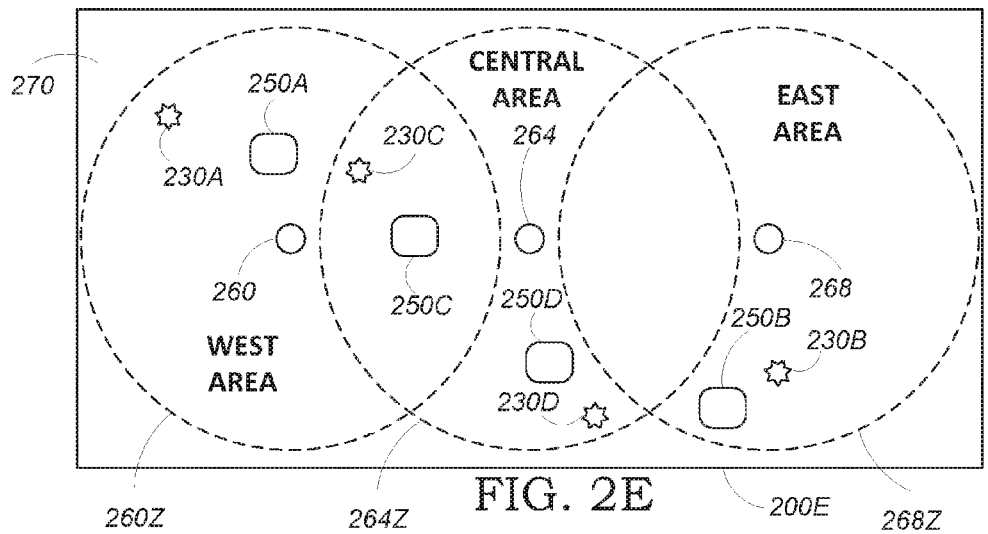

A specific case where using zone center beacons may be advantageous, is where zones are selected arbitrarily, and the borders among the zones are blurred, as will be clarified with reference to the exemplary floor layout 200E of FIG. 2E.

A large hall 270 is arbitrarily divided into three partly-overlapping zones: West Area 260Z, Central Area 264Z and East Area 268Z. Three zone center beacons 260, 264 and 268 are fixed to the ceiling at the centers of the respective zones. A staff member bearing a tag, such as tag 250A, happens to currently visit large hall 270. Upon tag 250A detecting zone center beacon 260 (or that the strength of the signal received from zone center beacon 260 exceeds a predetermined threshold), tag 250A locates itself as being currently located within West Area 260Z, and upon detecting asset 230A (actually the beacon of asset 230A) is will author a greeting that locates asset 230A within West Area 260Z. It will be noted that tag 250C will locate itself at both West Area 260Z and Central Area 264Z, and accordingly may author a greeting locating asset 230C at both West Area 260Z and West Area 264Z. It will be also noted that asset 230C will be located at West Area 260Z by tag 250A. A recipient of greetings from both tag 250C (locating asset 230C at both West Area 260Z and Central Area 264Z) and tag 250A (locating asset 230C at West Area 260Z only) may apparently locate asset 230C at West Area 260Z. Asset 230D will be detected by tag 250D as located at Central Area 264Z and asset 230B will be detected by tag 250B as located at East Area 268Z. It will be noted that tags 250A-250D may be separate tags borne by separate staff members, or be a single tag moved within large hall 270 by a staff member during routine work, being unaware of the asset locating activities and corresponding greetings sent by his or her tag.

It will be noted that location ambiguities may be tolerated, or even remain unnoticed by staff members who are directed to approach a located asset. For example, if a staff member is requested to approach asset 230C, directing her to either West Area 260Z or Central Area 264Z may prove very helpful, as long as she does not waste time in looking for the asset in East Area 268Z. Using homing for finding assets may further alleviate location ambiguities, as will be elaborated later below. The example of FIG. 2E highlights the fact that zones and borders may partly overlap and afford a certain level of ambiguity.

Figure 2F:
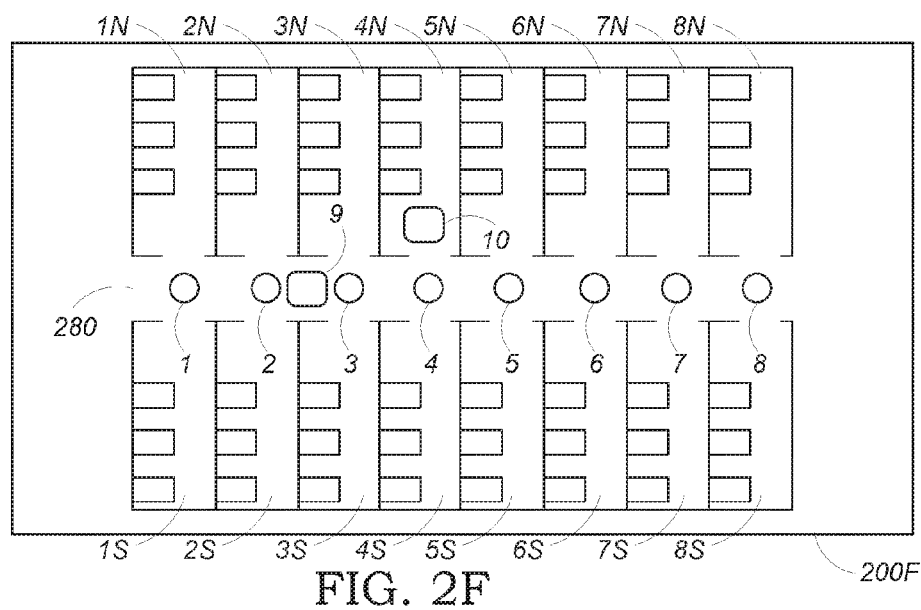

FIG. 2F schematically depicts another exemplary floor layout 200F, that includes sixteen rooms 1N-8N and 1S-8S, a corridor 280, and eight location beacons 1-8, that can be zone center beacons and/or zone border beacons, fixed to the ceiling and/or walls of corridor 280. Tag 9 identifies strong signals received from location beacon 2 and location beacon 3 and accordingly be located in "zone 2-3", while tag 10 receiving signals from location beacon 3, location beacon 4 and location beacon 5 may be located in "zone 3-5". Assets whose asset beacons are sensed by tag 9 or tag 10 (not shown in FIG. 2F) are reported as located in "zone 2-3" or "zone 3-5", respectively, which may be very helpful for a staff member sent to approach such assets. Thus, overlapping zones may still be very useful in practical applications, and such zones may be defined and named in advance, or ad-hoc according to the actual beacons detected by the tags. It will be noted, however, that signal strength analysis and self-learning may substantially narrow asset locating, for example locating tag 10 in "zone 4" instead of "zone 3-5".

Correlation Between Zone Sizes and Asset Beacon Signal Ranges

Locating an asset by a tag involves two primary stages: (i) identifying the tag's current zone, and (ii) detecting the asset via a short-range signal received by the tag from the asset's beacon. The conclusion of the two stages is that the asset is currently located at the tag's current zone.

Two parameters of interest to the present discussion that affect the effectiveness and dependability of the above locating process are the size of zones and the range of the short-range signal received by tags from asset beacons. Within the current section, the two parameters will be abbreviated "zone size" and "asset signal range", respectively.

The zone size can be arbitrarily determined by operational and cost considerations when implementing a system according to the present disclosure in a given site. The asset signal range is determined by factors such as: (i) the signal carrier, such as ultrasound, infrared or low-power RF; (ii) the strength of the signal transmitted by the beacon; (iii) the sensitivity of the tag's signal receiver; (iv) a threshold selected for ignoring weak signals received by the tag's signal receiver; and (v) the permeability of physical partitions that form part of the site, such as walls, to the signal transmitted by the asset beacon. Generally speaking, factors (i)-(iii) are a matter of design; factor (iv) allows dynamic range adaptation per site or even per zone, as well as calibration according to learning over time; while factor (v) is usually a given design constraint per site, unless extra partitions are purposely added for separating zones.

The following considerations may affect the design of specific embodiments of the present disclosure, as well as the settings of the signal threshold (iv) of the previous paragraph:

The asset signal range should be substantially smaller than the zone size, otherwise identifying the current location of a detected asset with the current location of the detecting tag may often be erroneous. An exception is when the zones are separated from each other by partitions (such as walls) that are impermeable to beacon short-range signals, which is better achieved with ultrasonic or infrared signals, or by shielding RF-permeable inter-zone partitions if RF signals are used. However, it should be noted that signals that are effectively blocked by partitions between zones, may also be blocked by partitions between rooms within a zone, or other random partitions, thereby highly reducing the number and frequency of useful locating reports, which may render the system less effective.

Operationally, larger zones imply reduced specificity when directing a staff member to an asset: "a respiratory machine at the West Zone on the 3rd floor" is less specific than "a respiratory machine next to bed C in room 305". It is assumed, however, that such reduced specificity is still good enough for directing staff members toward assets in many sites, which makes larger zones acceptable for such sites.

Smaller asset signal range reduces the number and frequency of useful greetings: A greeting is often authored and reported by a random passing-by tag who happens to detect an asset when moving in its proximity. A small asset signal range implies that some assets that are currently positioned in an area that is seldom visited, may not be detected by tags that pass-by.

Larger asset signal range introduces locating errors: signals transmitted by an asset positioned at a certain zone and received and reported by a tag at another zone (such signals will be called herein "leaks"), may introduce errors when directing a staff member to the asset, such as when directing the staff member to the West Zone instead of the South Zone because of an asset signal that penetrated a wall between the zones during the locating phase. Such error events may be remedied by using homing as part of the directing process, which will exploit the very leak that created the error for correctly directing the staff member toward the asset, or toward a wall behind which the asset is hiding; also, the staff may get used to a certain low percentage of direction errors and learn to overcome such errors by searching an unfound asset at a neighboring zone.

Resolving conflicting greetings by the recipient: in a busy site, the recipient of the greetings, such as a site database or an asset manager's portable terminal (see FIG. 4E below)

may receive a plurality of greetings pertaining to the same asset from different tags within a short period of time. Preferably, the strength of the beacon signal received by the tag is included in the greeting (see item (4) in FIG. 4D below), and then greetings associated with stronger signals are considered more significant. Also, in case that there is only a single greeting and it is associated with a weak signal, the tag zone may be then presented as approximate location when directing a staff member to the respective asset.

It will be appreciated that experience and self learning may assist in: (i) fine-tuning the zone allocations (and possibly lead to repositioning some respective zone border or zone center beacons, if used); (ii) calibrating the relative weights of location signal strengths received by the greetings recipient; and (iii) the staff members learning to tolerate sporadic direction errors.

Locating People

The system described above uses tags borne by and moving with people to locate assets via their attached beacons. Tags are typically borne by staff members, but can be also be borne by residents, customers and/or visitors.

Locating a person as being in a certain zone via locating his or her tag is often useful by itself. Such tag location is reported by default as part of a greeting (see FIG. 4D), and can also be reported independently of a greeting, for example whenever crossing the border between zones.

Since people may move a lot, real-time reporting is important, which requires continuous network communication availability, at least next to the passages between zones.

Frequency and Validity of Greetings

A greeting is preferably timestamped and authored upon a tag detecting an asset. However, the greeting can be forwarded by the tag only when network communication is available. In addition to availability, communication cost and bandwidth may push toward batching several greetings to be sent as a single message.

Assets are usually stationary during service or storage, and therefore a greeting may be considered valid for minutes or even hours from its time stamp. A greeting expiration time may be set according to an asset type and calibrated by experience; however, in the absence of a fresher greeting, the last greeting received from an asset may be used even past its expiration time.

A tag that remains in proximity to an asset may detect numerous signals transmitted by the asset. Following authoring a greeting, subsequent signals from the same asset may be ignored for a predetermined period of time, say two minutes, or until a zone change is detected, for example when the asset is moved from one zone to another by the tag bearer.

The more timely a greeting is, the more dependable is the respective asset locating data. Accordingly, if available and affordable, continuous network coverage throughout the site is highly preferred.

The Locating Process

Figure 4A:
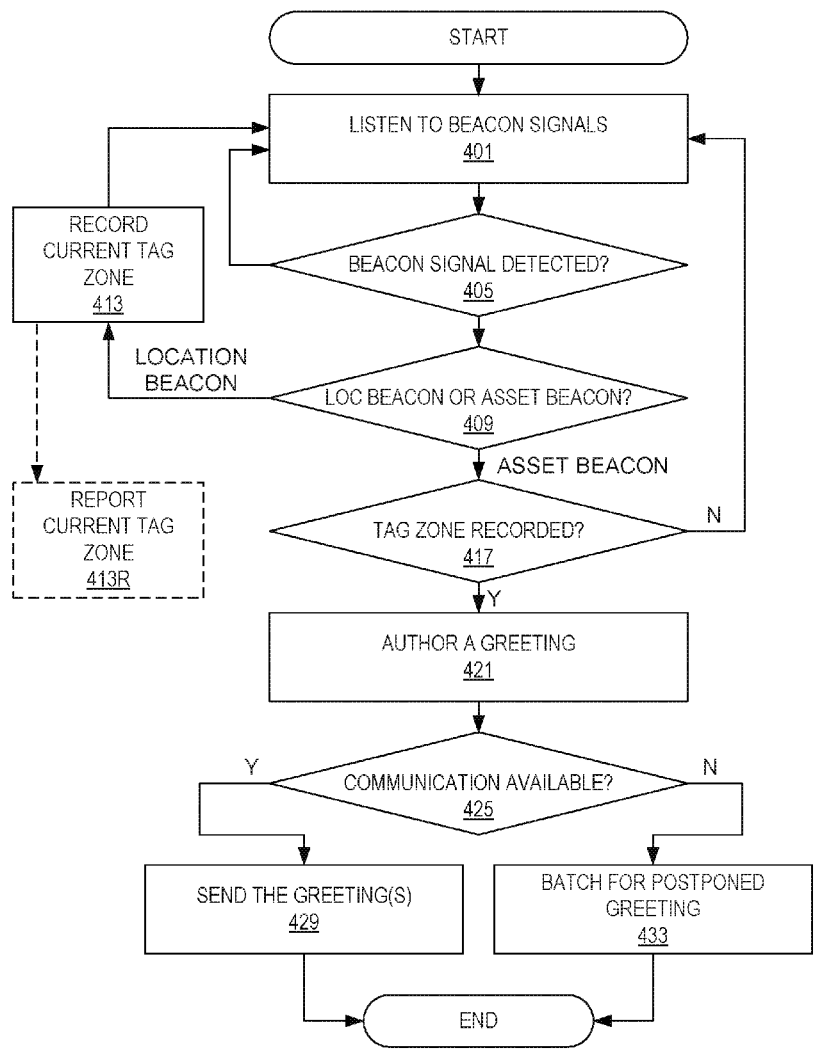
FIGS. 4A-4C are flowcharts describing asset locating processes according to preferred embodiments of the present invention.

FIG. 4A describes an asset locating process by a tag, in a site that includes location beacons for locating the tag within a zone (for example, as described in FIG. 2B, 2D or 2E). In step 401 the tag listens to beacon signals that may arrive from location beacons (zone border beacons or zone center beacons) or from asset beacons. If in step 405 a beacon signal is detected, then step 409 checks whether the detected signal is from a location beacon or and asset beacon. In case of a location beacon, the current tag zone as determined from the location beacon is recorded in step 413 in the tag's memory, and, if locating persons is implemented and communication is available, then in optional step 413R the current tag zone is reported to the designated recipient (FIG. 4E).

If step 409 determined that the beacon signal is from an asset beacon, then step 417 checks whether that tag zone is recorded in the tag memory as a result of a previous loop via step 413, and if so, a greeting is authored by the tag in step 421, followed by step 425 checking whether communication is available. If communication is available, then in step 429 the greeting authored in step 421 is sent to the designated recipient, possibly along with previous unsent greetings; otherwise the greeting is batched in step 433, for being sent when communication is available.

Figure 4B:
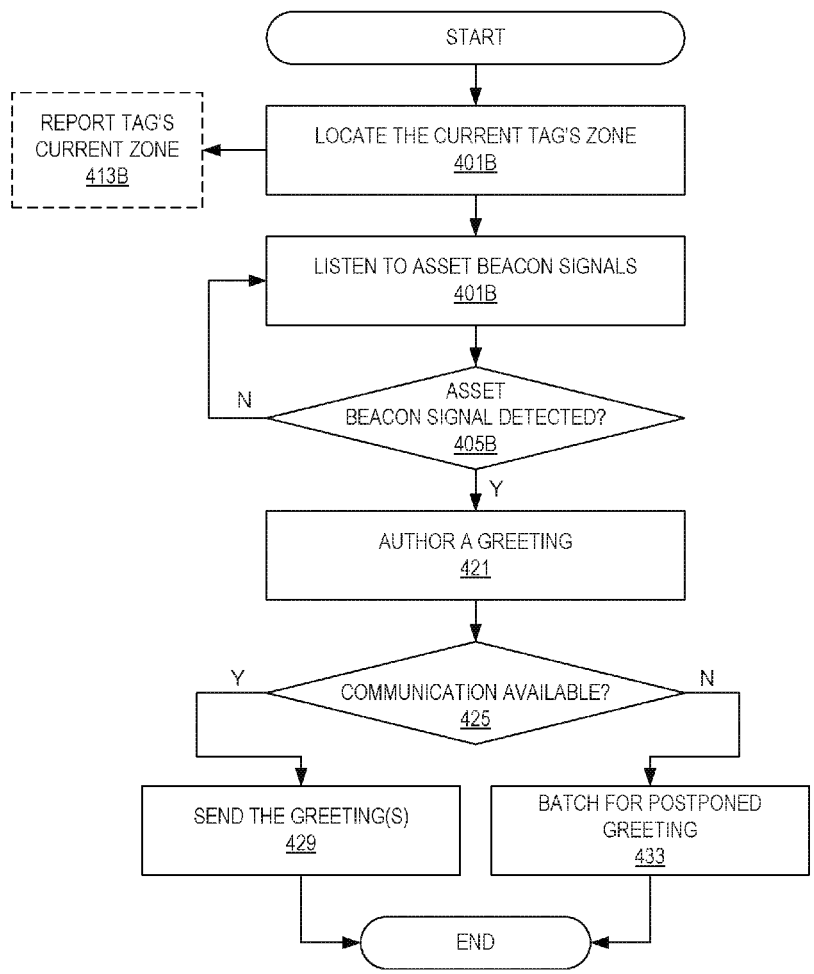

FIG. 4B describes an asset locating process by a tag using any tag's zone locating method. Thus, in step 401B the tag's current zone is located using any tag locating method, such as the beacons in FIG. 2B, 2D or 2E; or the turn analysis and/or visual features of FIG. 2C; or by detection and analysis of irregularities in the earth's magnetic field of U.S. Pat. No. 8,798,924 depicted above; or any other applicable indoor positioning method. In optional step 413B, the tag's current zone is reported if locating persons is implemented and communication is available. In step 401B the tag listens to asset beacon signals. If in step 405B an asset beacon signal is detected, then a greeting is authored in step 421. If step 425 finds out that communication is available, then in step 429 the greeting authored in step 421 is sent to the designated recipient, possibly along with previous unsent greetings; otherwise the greeting is batched in step 433, for being sent when communication is available.

Figure 4C:
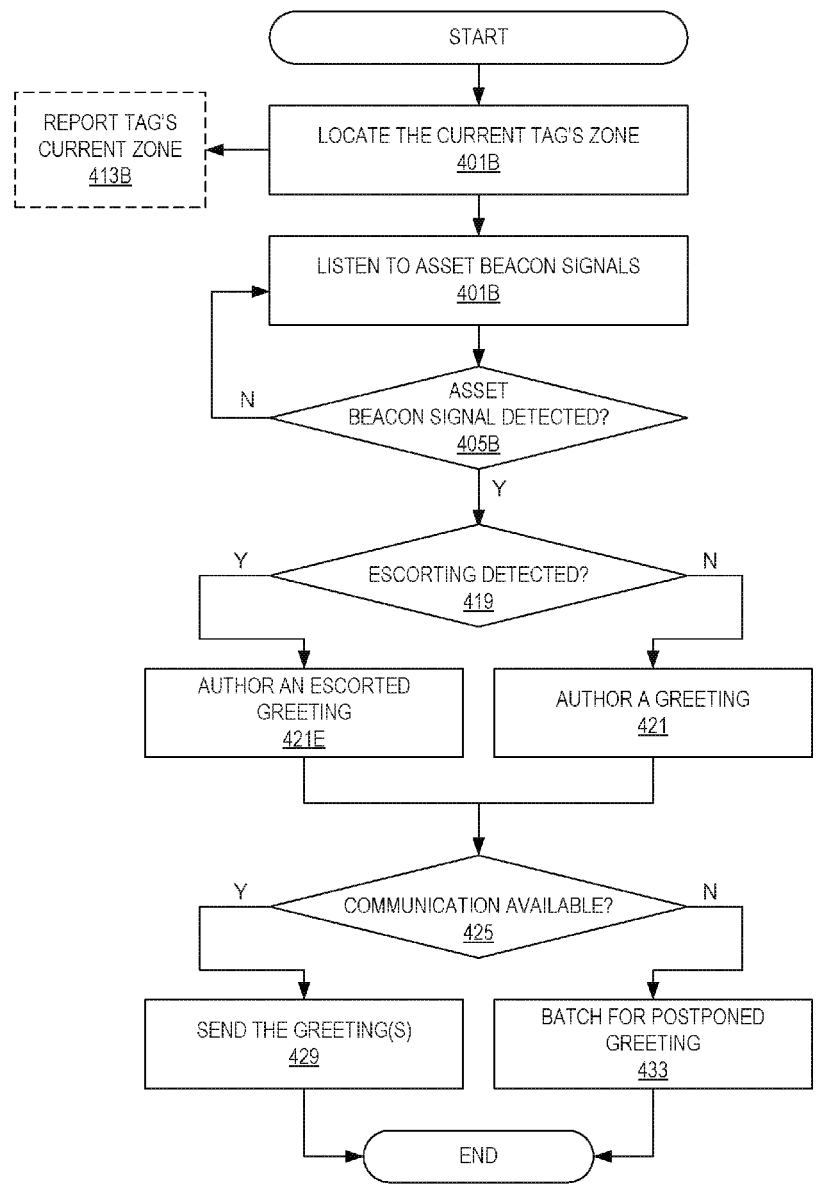

FIG. 4C describes an asset locating process similar to the process of FIG. 4B, while also checking and reporting escorting events. Thus, in step 401B the tag's current zone is located using any tag locating method. In optional step 413B, the tag's current zone is reported if locating persons is implemented and communication is available. In step 401B the tag listens to asset beacon signals. If in step 405B an asset beacon signal is detected, then in step 419 the tag checks whether the tag and the detected asset are in escorting mode, which is when the tag and the asset maintain a closed proximity for a duration of at least a predetermined period of time, such as thirty seconds, and the tag detects that it has moved during that period, such by detecting change of zone or according to motion detection by an accelerometer included in the tag's sensors 138 (FIG. 1). If escorting is not detected, then a greeting is authored in step 421; otherwise is step 421E, a greeting message that include escorting information (FIG. 4D) is authored. If step 425 finds that communication is available, then in step 429 the greeting authored in step 421/421E is sent to the designated recipient, possibly along with previous unsent greetings; otherwise the greeting is batched in step 433, for being sent when communication is available.

Greeting Contents

Figure 4D:
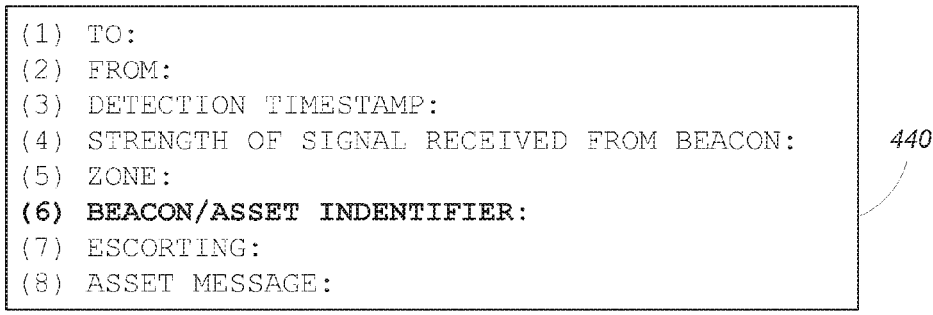
FIG. 4D is a schematic illustration of the contents of a greeting according to a preferred embodiment of the present invention.

FIG. 4D schematically describes the contents of a greeting 440 sent by a tag to a recipient, to report that the tag has detected asset X in zone Y. Out of fields (1)-(8) of the greeting, only field (6)—the identity of the detected asset—is mandatory, while the other seven fields may be optional, implicit, or otherwise available to the recipient.

Field (1) identifies the greeting recipient or recipients (see FIG. 4E) which may be the same for all greetings in the site (e.g. a site server) hence redundant. Field (2) identifies the sending tag, which may be also derived from the network communication protocol hence redundant. Field (3) indicates the time when the tag detected the presence of the asset, which may be essentially identical to the time of receiving the message by the recipient, if real-time communication is implemented. Field (4) reports the strength of the beacon's signal detected and measured by the tag, if this feature is implemented; weaker signals may indicate larger distance and/or obstructions between the tag and the beacon, which may assist the recipient in deciding between conflicting greetings received at a similar time from different tags and locating the same asset at different zones.

Field (5) reports the zone where the asset is located, which is the zone where the tag is or has been located at the moment of detecting the tag's location. In implementations of the present disclosure where persons are continually located by their tags and where greetings are sent in real-time, the current zone of the tag may already be known to the greeting recipient, which may make field (5) redundant.

Mandatory field (6) identifies the detected asset, directly or via identifying the respective beacon attached to the asset, such as by inventory number an/or detailed description.

Field (7) indicates whether the greeting is produced in connection with an escorting event (FIG. 4C) which usually suggests that the detected asset has been moved by the tag bearer. Such information can be useful in various ways: (a) identifying unauthorized moving of assets; (b) referring questions regarding the current location of the asset to the respective tag bearer; (c) identifying the current mover as the preferred mover for the next moving of the same asset, since the current mover is already familiar with the current location of the asset within the zone; or (d) if the reporting tag is borne by a designated mover of the asset, the asset may be presumed to have been relocated to the designated moving target location, such as "next to bed C in room 305".

Field (8) is for implementations where the asset beacon 150 includes and employs an asset interface 158 for receiving status messages from the asset, such as usage, material inventory or need for maintenance. Such messages are included in field (8) to be handled by the message recipient.

Recipients of Greetings

A greeting is intended to update a location data store 170 of a recipient, as to where the respective asset is located. FIG. 4E schematically introduces three typical recipients that may benefit from receiving greetings.

In a common scenario, greeting-sending tag 450 addresses its greetings to site server 458 such as a central hub of administrative information in the site. Any would-be user of asset location information may then connect with site server 458 for retrieving the requested information.

Alternatively or additionally, in sites that employ an asset manager who is in charge of assets, greetings may be sent to asset manager's portable terminal 454, such as a tablet, mobile phone, or an enhanced staff tag, to allow the asset manager to conveniently and continuously monitor all assets.

Alternatively or additionally, in sites that employ staff members who are often assigned moving tasks, an extended asset mover's tag 462 may receive greetings from greeting-sending tags 450, so that when the mover is sent to urgently fetch "the yellow respiratory machine" he'll have the respective location information readily-available at hand in his own staff tag. Optionally, such location data may be retrieved on-demand, by asset mover's tag 462 sending a query to all tags, which can be informally described as asking all tags "who has seen the yellow respiratory machine during the last hour?", which is then responded by greetings sent from only the tags which have recently detected the sought asset.

Escorting

Figure 5:
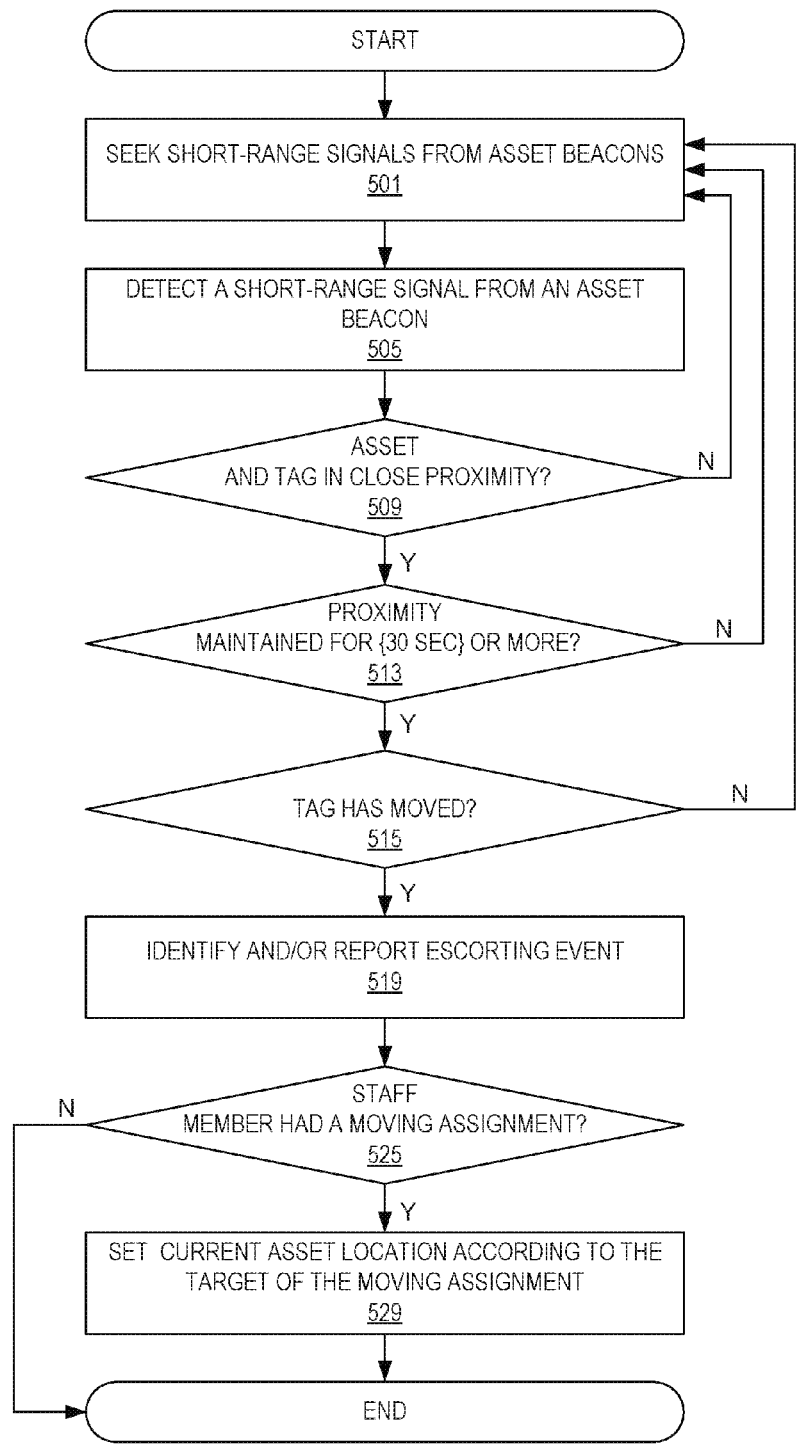
FIG. 5 is a flowchart depicting the detection of escorting events according to a preferred embodiment of the present invention.

FIG. 5 further elaborates on escorting events depicted above with reference to steps 419 and 421E of FIG. 4C.

Detection of escorting events comes to identify that an asset is moved by a tag bearer, usually a staff member. A first condition for escorting is learning, from the asset beacon signal received by the tag, that the asset and the tag are in close proximity. To avoid false detection of an escorting event when the tag just passes by the asset, a second condition for escorting is ensuring that the close proximity is maintained for a prolonged duration, such as 30 seconds or more. To further avoid false detection in case that a staff member happens to stand in close proximity to an asset for a prolonged time, such as a nurse standing next to an asset while taking care of a resident, a third condition is detecting that the tag, apparently together with the asset, have moved while maintaining the close proximity.

In step 501 a tag seeks signals from asset beacons and in step 505 an asset beacon is detected. Step 509 learns from the strength of the signal received from the asset beacon whether the asset and the tag are in close proximity, such as a meter or less. If yes, then step 513 checks whether the close proximity is maintained for a prolonged duration, such as thirty seconds or more. If so, then step 515 checks whether the tag has moved while the closed proximity has been maintained, for example by detecting that the tag has crossed a border between zones and/or by consulting an accelerometer or camera included in sensors 138 of the tag. A positive outcomes in all three steps 509-515 identifies an escorting event, which implies that the asset has been moved by the tag bearer, which conclusion is identified and/or reported in step 519. Step 525 checks whether the staff member bearing the tag had a moving assignment for the detected asset, and if yes, then step 529 sets the current location of the asset according to the target of the moving assignment, such as next to bed C in room 305, which is more specific than locating the same asset at the West Zone as in the general locating case.

Figure 4E:
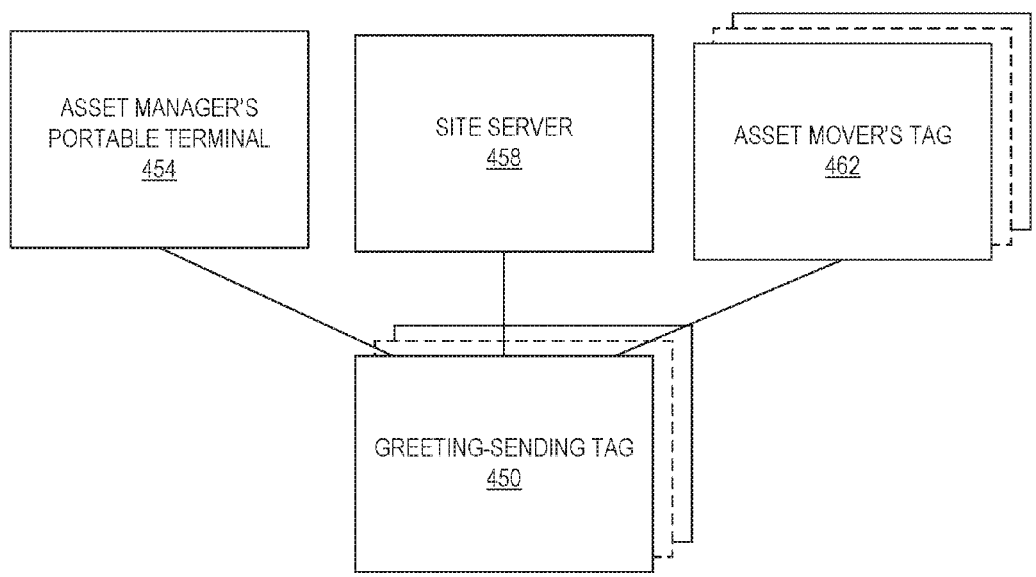
FIG. 4E is a block diagram depicting distribution of greetings according to preferred embodiments of the present invention.

It will be appreciated that while steps 501-515 are performed by the tag, steps 519-529 may be performed by the tag, or, additionally or alternatively, by recipients to which the tag reports, such as site server 458, asset manager's portable terminal 454, or asset mover's tag 462 of other movers (see FIG. 4E). In any case, the end result of the process is that the current location of the moved asset is updated to be the target location specified in the moving assignment.

Directing a Staff Member Toward a Tag

Figure 6:
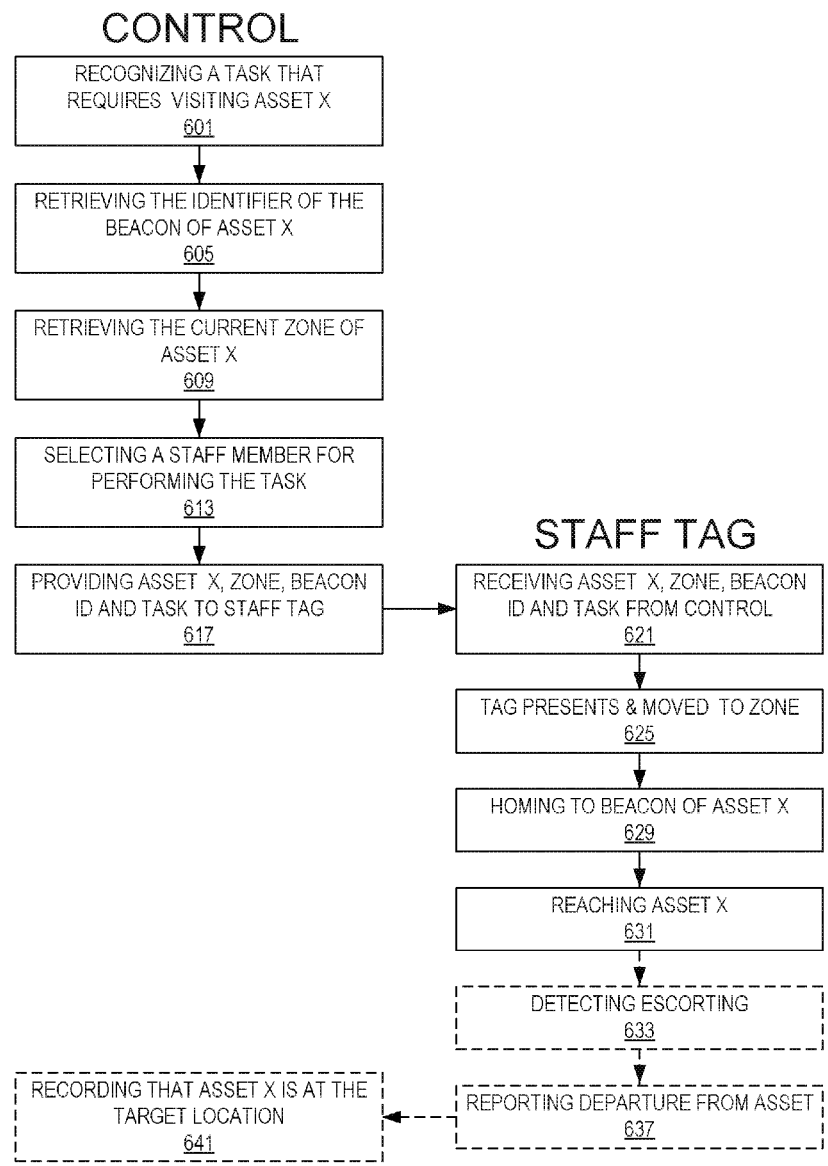
FIG. 6 is a flowchart depicting a process of directing a staff member toward an asset according to a preferred embodiment of the present invention.

FIG. 6 describes a process of directing a staff member toward an asset for performing an asset-related task, such as repairing, replenishing supplies, moving the asset to a new location, or just visiting the asset by a security attendant. The steps on the left hand side of the chart are performed by a control computing device (see control 174 in FIG. 1A), while the steps on the right hand side are performed by the tag of a staff member designated to approach the asset.

In step 601 control generates or receives a task that requires visiting a specific asset, herein called asset X. Generation of a task by control can be made automatically for repair, replenishment or security tasks, or entered manually into the control by a supervisor, for example when the asset is needed in a certain place, in which case the task is an asset relocation task. In step 605 control retrieves the identifier of the beacon attached to asset X, for example from location data store 170 of FIG. 1A, and in step 609 control retrieves, also from location data store 170, the current zone of asset X most recently reported by a locating process, such as the processes of FIG. 4A-4C or 5 above. In step 613, a staff member is selected for performing the task, which can be made automatically, for example where there is just a single staff member on duty that is suited for the task, or via a manual input received by control from a supervisor. In step 617, the description of asset X, the current zone of asset X, the respective beacon identifier and the task description are provided by control to the staff tag of the selected staff member.

Figure 7A:
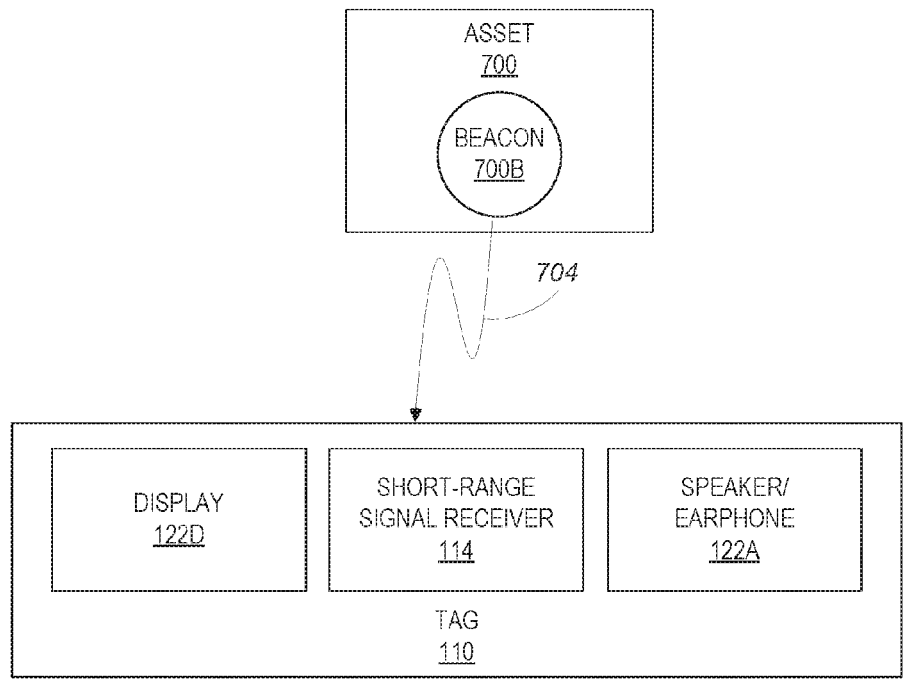
FIGS. 7A-7C are schematic illustrations that pertain to homing, according to preferred embodiments of the present invention.
Figure 7B:
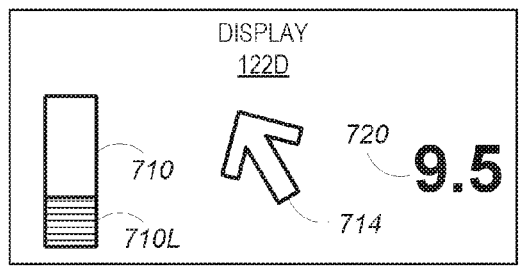
Figure 7C:
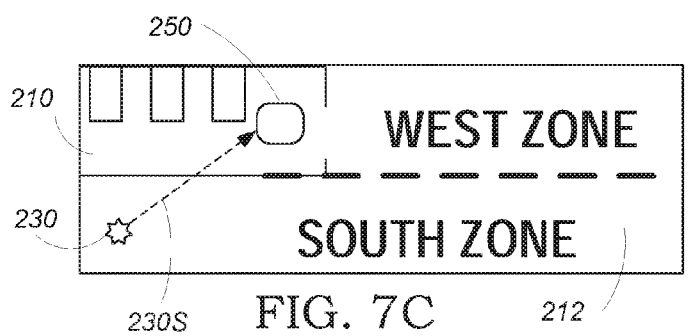

In step 621 the staff tag of the selected staff member receives the data provided by control in step 617. In step 625 the tag presents the zone to and is moved to the zone by the staff member who bears the tag. Step 629 initiates a homing process, in which the tag seeks signals that carry the beacon identifier, and when such signals are detected, the tag guides the staff member toward the asset by providing homing indicia toward the beacon (FIGS. 7A-7C below). In step 631 the tag reaches asset X, which enables the staff member to perform the task.

Steps 633-641 pertain to the case where the assigned task is moving the asset to a new target location. In this case, in step 633 the tag detects an escorting event, which implies that the asset is moved by the staff member who bears the tag. In step 637 the tag detects, from the weakening or disappearance of the beacon signal, the departure of the staff member from the asset hence the purported completion of the moving task, which lets control, in step 641, to record the new location of asset as the target of the moving task.

Homing

FIGS. 7A-7C summarize and highlight some aspects relating to homing, in addition to aspects pertaining to homing presented in previous sections. FIG. 7A presents an asset 700 to which an asset beacon 700B is attached. Asset beacon 700B recurrently transmits short-range signal 704, such as an infrared, ultrasonic or a low-power RF signal, which is received by short-range signal receiver 114 of tag 110. Tag 110 interprets short-range signal 704 for both identifying asset beacon 700B and measuring the strength of the received signal, which is generally proportionate to the distance between the tag and the asset. Display 122D and/or speaker/earphone 122A serve to provide visual and/or audio indicia of the current measured signal strength, which serve to guide the staff member who carries the tag toward the beacon, hence toward the asset. FIG. 7B schematically describes indicia displayed on display 122D of tag 110. Thus, text 720 displays the signal strength in numeric terms, preferably using distance units for presenting the estimated distance between the tag and the asset derived from the signal strength; signal level bar 710 shows graphically current signal level 710L; while beacon pointer 714 show the estimated beacon direction, derived from a series of signal strength readings during the motion of the tag in combination with readings from a compass and/or accelerometer included in sensors 138 (FIG. 1A).

FIG. 7C schematically demonstrates how homing may remedy locating errors, using a scenario based on the southwest corner of the floor layout of FIGS. 1A-1B. An asset 230 is located in a corridor 212 that is very rarely visited by tag-bearing persons. The corridor 212 has been assigned to the South Zone, while a frequently-visited neighboring room 210 has been assigned to the West Zone. The wall between room 210 and corridor 212 is sufficiently permeable to RF asset beacon signal 230S to allow a tag 250 visiting room 210 to detect asset 230. During the locating phase, several tags visiting room 210 mistakenly report that asset 230A is located at the West Zone, and its correct location in the South Zone is not reported simply because no tag happens to visit the deserted corridor 212. However, when a staff member is directed to visit asset 230 in the West Zone, he uses his tag 250 to quickly screen all the rooms of the West Zone, including room 210. When in room 210, tag 250 detects asset 230 via RF asset beacon signal 230S, and the homing process directs the tag bearer toward the wall, which will lead most reasonable staff members to search and find asset 230 behind the wall, in corridor 212 that belongs to the South Zone. Thus, the very leak that causes the locating error during the locating phase, helps to recover from this error during the directing phase.

Blind Areas

Figure 8A:
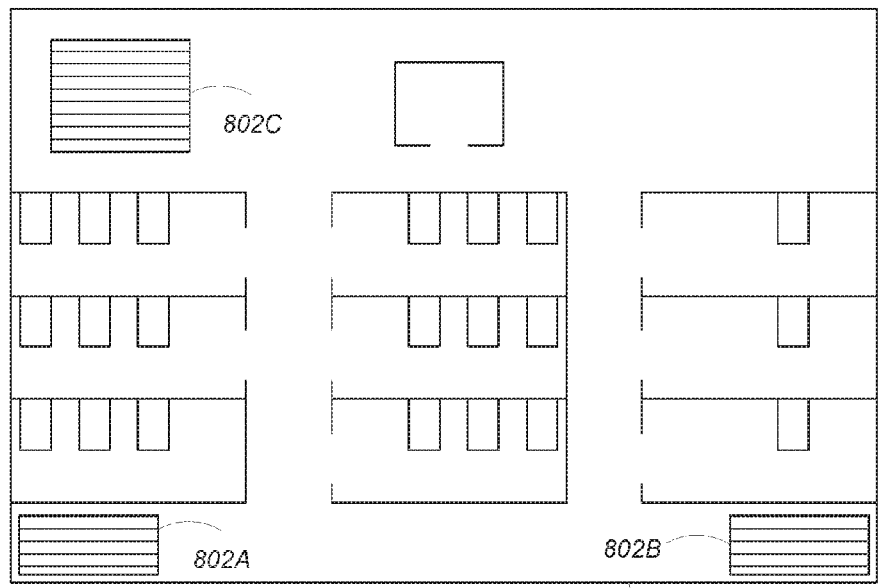
FIGS. 8A-8B are schematic illustrations that describe floor layouts that include blind areas.

A "blind area" is an area that may host assets but is seldom or never accidently visited by passing-by tags. FIG. 8A schematically describes floor layout 800A that includes blind area 802A and blind area 802B that are positioned at dead ends of a corridor and are visited just once a day by the cleaner, while blind area 802C is a closet or a storage room that may store assets.

Blind areas may collectively form a "blind zone" that is systematically screened by staff members when an asset is not found in its last reported location, or security personnel or other staff members may be directed to periodically, say once per hour, pass through all blind areas. Such a security screening may also be initiated when a certain asset is not reported by any greeting during an extended period of time, say three hours. Alternatively, an asset beacon detector 820 may be used to cover a blind area, as described below with reference to FIG. 8B.

Security and Beacon Detectors

It is a clear interest of a site to prevent assets from being stolen or misplaced to another floor or section.

Beacons should preferably include tamper-detection sensors, that turn on an audible alarm and/or turn the beacon's short-range signal into an alarm signal. Accordingly, routinely locating an asset within its designated area verifies that the asset has not been misplaced or stolen.

On the other hand, failure to locate an asset for extended time may imply either that the asset has been misplaced or stolen, or that the asset is currently located in a blind area. Both situations can be preempted by deploying beacon detectors in selected areas.

A "beacon detector" is essentially a tag that is fixed at a selected location, such as a ceiling or a wall, for detecting assets in its proximity. Its design is similar to tag 110 of FIG. 1A, modified for continuous operation in a fixed location, which implies continuous network connection and preferably drawing energy from the site's electrical network.

Figure 8B:
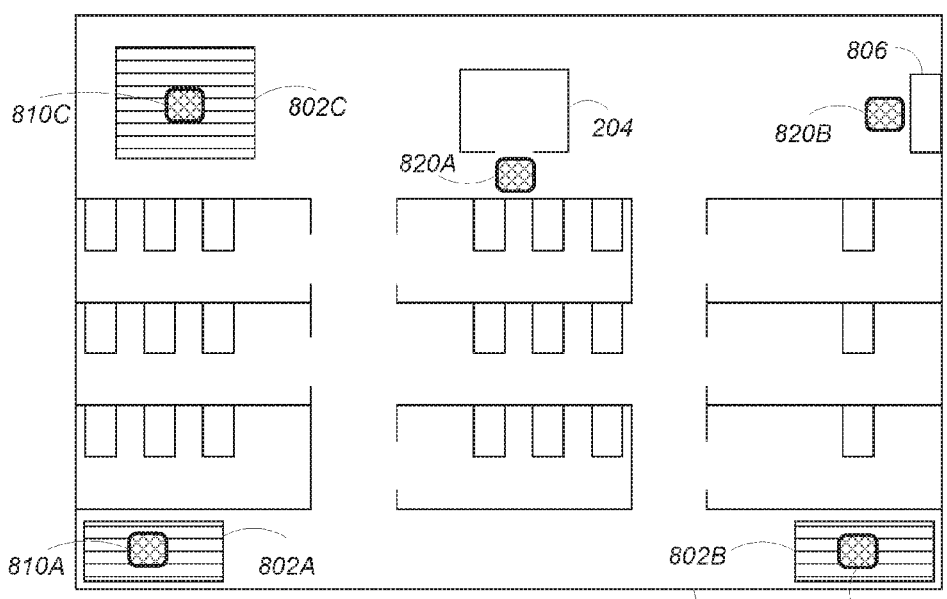

FIG. 8B describes a floor layout 800B that employs beacon detectors for timely locating and detecting assets. Floor layout 800B has two exits: elevator 204 and staircase 806. Security beacon detectors 820A-820B are preferably fixed next to the exits, and upon detecting an approaching asset and checking that moving the asset has not been authorized, the event is reported, an alarm may be triggered and/or the respective exit may be locked. Beacon detectors 810A-810C are fixed in the blind areas 802A-802C of FIG. 8A, and periodically report the location of assets that are contained within the blind areas.

Multi-Function Smart Devices

The active devices discussed so far can be divided into:
(a) tags borne by persons for detecting beacons,
(b) location beacons for assisting tags in locating themselves within zones,
(c) asset beacons for being detected by tags, and
(d) fixed beacon detectors that are tag-like devices fixed within blind areas or at exits.

In some embodiments it may be advantageous to combine several tag/beacon functions into a single enhanced smart device as described below.

Figure 9A:
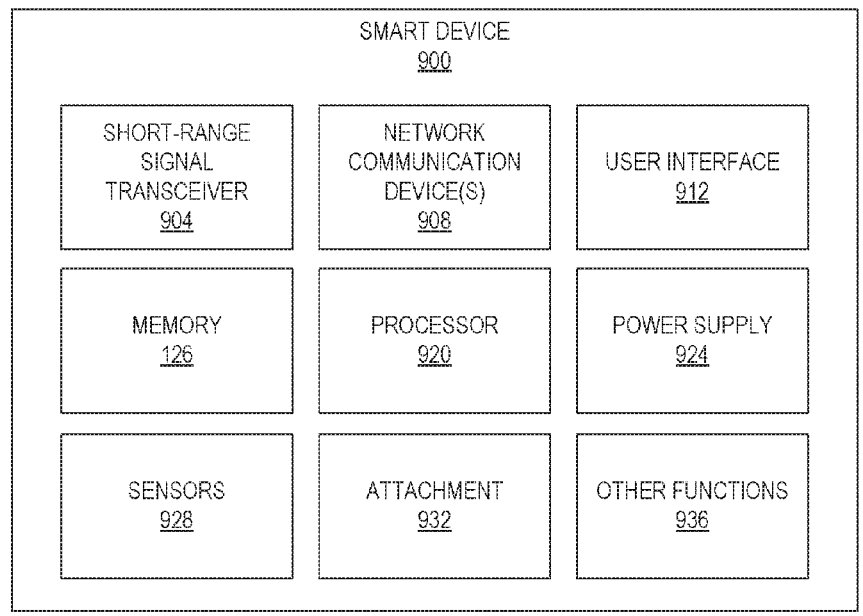
FIG. 9A is a block diagram of an enhanced smart device according to a preferred embodiment of the present invention.

Referring to FIG. 9A, smart device 900 is devised to serve as an enhanced tag or enhanced fixed beacon detector. Short-range signal transceiver 904 may act, in addition to receiving short-range signals as in the case of short-range signal receiver 114 of tag 110 in FIG. 1A, also as a short-range signal transmitter, allowing smart device 900 to act also as a beacon. Network communication device(s) 908 may be enhanced to not only act as a network connection means that serves tag 110, but also as an access point that serves other smart devices that lack a continuous network connection of their own and pass by smart device 900; for example, network communication device(s) 908 may use both a cellular network connection and a local Wi-Fi or Bluetooth link to offer a cellular hotspot to passing-by smart devices. User interface 912 may be reduced or eliminated in comparison to user interface 122 in case that smart device 900 is fixed to a location. Processor 130 is enhanced, compared to processor 130 of tag 110, to accommodate the added functionalities described herein. In case of a fixed installation, power supply 924 may draw power from the site's electrical network, and sensors 928 may be eliminated or reduced to camera-only, for example. Attachment 932 may be suited for fixed installation, while other functions 936 may be nullified in case that smart device 900 is dedicated solely to location-related functions.

Figure 9B:
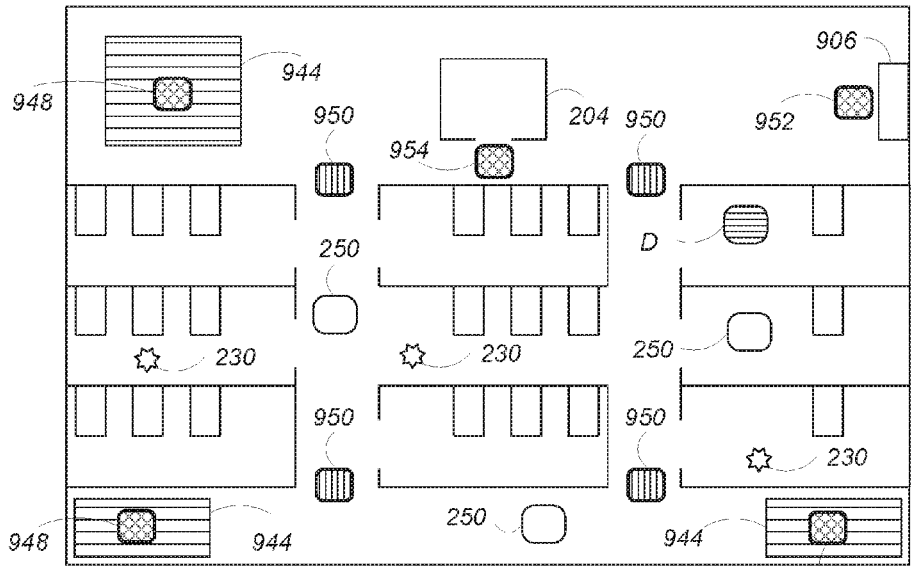
FIG. 9B is a schematic illustration that depicts a floor layout for demonstrating exemplary smart device implementations.

FIG. 9B uses a floor layout 940 for demonstrating several exemplary smart device implementations. Smart devices 948 are positioned in blind areas 944 for detecting assets and reporting their location. A smart device 948 is preferably fixed to the wall or ceiling within or next to the respective blind area, and is preferably equipped with continuous network connection and draws power from the site's electrical network. Smart device 954 is positioned next to the elevator door and may serve several functions: (i) a zone border beacon for allowing tags locate their entry into or exit from the Elevator Zone; (ii) a security object detector for detecting objects that are not permitted to leave the zone without suitable escorting; (iii) a network communication access point allowing passing-by tags establish network connection. Smart device 952 may be similar to smart device 954, preferably except the beacon functionality. Smart devices 950 in a minimal configuration may operate as both zone border beacons (see 220A-220D of FIG. 2B) and access points that provide network communication to tags upon crossing borders between zones, which implies continuous zone-level locating of all tag-bearing persons crossing the respective borders. Smart devices 950 may be further enhanced, to act also as beacon detectors, in which case zone-level locating of all assets can depend on smart devices 950+954 alone, thereby obviating that need for locating and greeting activities by moving tags 250. It will be appreciated, however, that in order to depend solely on smart devices 950 for asset location, continuous electricity and communication supply to smart devices 950 become mandatory, which requires substantially more investment in infrastructure modifications, compared to when using zone border beacons as in floor layout 200B of FIG. 2B, since beacons can operate for months and years on battery power and the configuration of FIG. 2B does not mandate continuous communication at each location beacon. Accordingly, in some cases an installation of a locating system according to the present disclosure can start with zone border beacons 220A-220D of FIG. 2B, and be later upgraded by supplementing or replacing zone border beacons with smart devices 950 of FIG. 9B, which may be made gradually or at once. Smart device 958 is essentially identical to tags 250, with the addition of a mobile access point, such as a mobile Wi-Fi hotspot that connects to the network via cellular communication, for serving simpler passing-by tags that have no cellular communication of their own.

Multi-Level Border Control

Asset security has been discussed above with reference to FIG. 8B, where security beacon detectors 820A+820B positioned next to the exits from the floor area detect approaching assets and trigger an audible alarm and/or lock the respective exit upon finding out that moving the asset out of the floor area has not been authorized. It will be appreciated that such alarm or exit lock events may be annoying to uninvolved persons in the area, and the following arrangement comes to reduce the frequency of such annoyance by earlier detection and preemption of such events.

The forthcoming discussion covers locating and securing both assets and persons, and will therefore relate to locating and securing "restricted objects" that require authorization in order to move or be moved out of a predefined area, called herein a "confined area". Restricted objects can be "restricted assets" that are supposed to stay at a predefined confined area, or persons, such as certain residents ("restricted residents") in a healthcare facility, that require special attention and supervision.

Figure 10A:
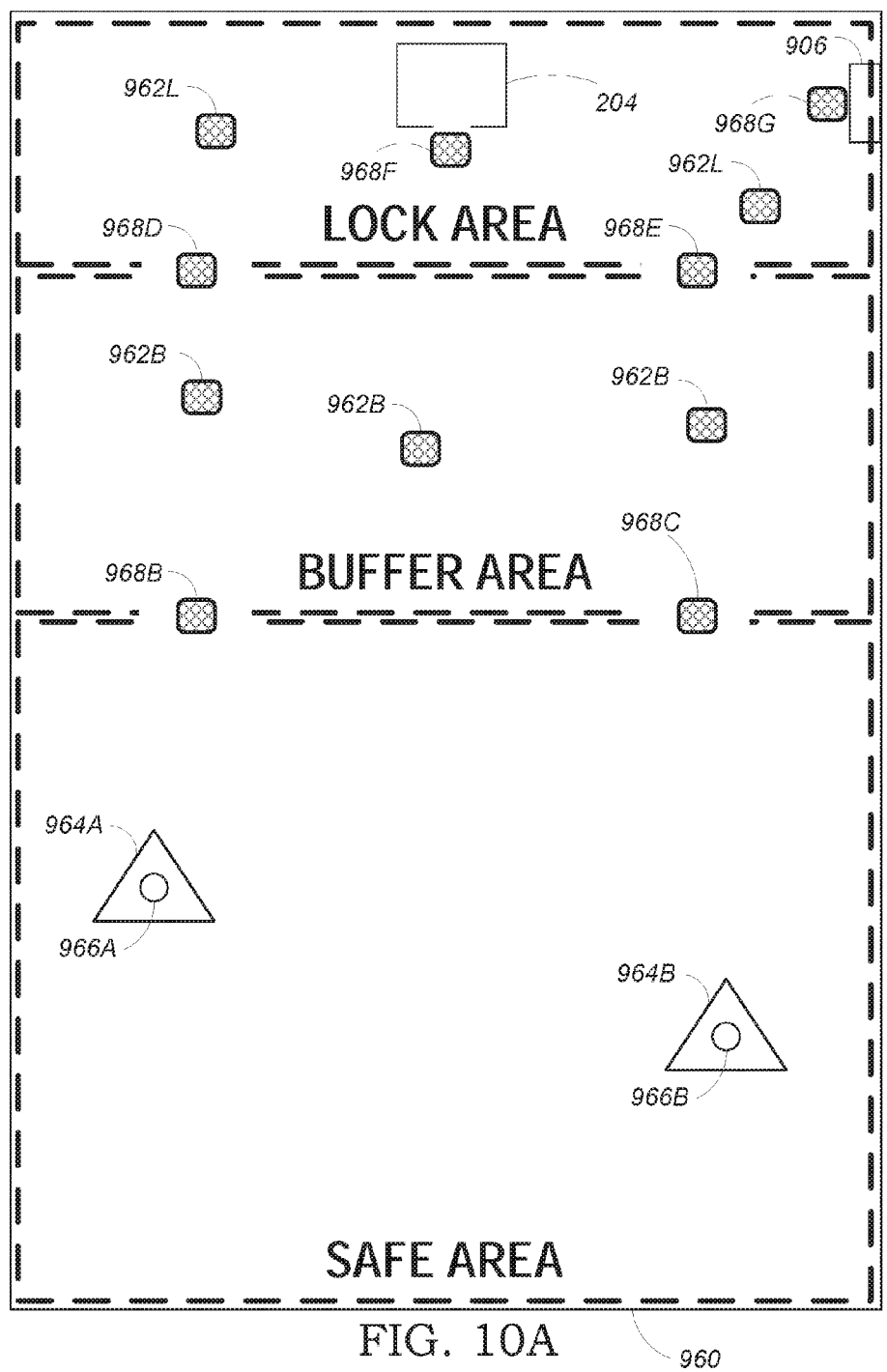
FIGS. 10A-10C are schematic illustration of floor layouts that pertain to multi-level border security.

FIG. 10A depicts a of a confined area 960 that accommodates restricted object 964A and restricted object 964B, each can be an asset or a person that is designated to normally stay only within the safe area. The term "area" is used herein to avoid confusion with the term "zone" used above, and it will be appreciated that both zones and areas may be used concurrently in sites that implement both general locating as depicted above, and the security feature discussed hereinbelow. A "buffer area" is an area where a restricted object is not supposed to stay without authorization, but is otherwise harmless. Authorization may be in the form of a temporary permit received from a senior staff member, or by recognizing that the object is accompanied by an authorized person, such as a designated staff member or a trusted family member identified by his or her tag or beacon. Such escorting may be recognized by a tag of a authorized person or of a restricted object that detects that close proximity is maintained between the authorized person and the restricted object for an extended period of time, similarly to detecting escorting events according to FIG. 5, or by detecting simultaneous proximity of both a restricted object and an authorized person to a fixed tag or beacon. The buffer area is preferably used to provide an early warning and early intervention opportunity for staff intervention, in case that a restricted object is detected entering or within the buffer area without authorization. If a restricted object further moves or is moved through the buffer area and is detected to appear without authorization at the "lock area", some or all exits from the lock area, such as elevator 204 and/or the door of staircase 906, automatically lock, possibly selectively according to that detected location of the restricted object, to minimize annoyance to uninvolved persons. If, for one reason or another an exit fails to lock, as may occur in the case of "tailgating", i.e. a restricted person following an unrestricted person while keeping the exit open, the restricted object enters without appropriate escorting the "alarm area", which is not explicitly marked in FIG. 10A, and consists of the elevator 204 and the staircase 906, which triggers an alarm. It will be appreciated that a generous buffer area will effectively eliminate the great majority of exit locking events, while a sufficient lock area may turn alarms into extremely rare occasions. It will be noted that in a certain embodiments, different restricted objects or groups of restricted objects within the same floor may be allocated separate safe areas, in which case safe areas and buffer areas may be individually allocated for such objects or groups of objects.

It will be appreciated that the terms safe area, buffer area, lock area and alarm area defined above are used for brevity and clarity, and represent concepts that may be described and elaborated using alternative terms without deviating from the underlying structural, logical and operational concepts.

In the embodiment of FIG. 10A, object beacon 966A is attached to restricted object 964A while object beacon 966B is attached to restricted object 964B, where the term attached preferably means physical attachment in case of an asset, or a convenient wearing or carrying arrangement in case of a person, with tamper-detection means possibly implemented in both cases. Fixed tag 968B and fixed tag 968C are positioned at the passages between the safe area and the buffer area for detecting entry of a restricted object into the buffer area. Optionally, additional fixed tags 962B may be scattered within the buffer area to detected restricted objects with the buffer area. Possibly, in some implementations, fixed tag 968B and fixed tag 968C, as well as fixed tags 962B, may also be configured to autonomously detect and select nearby staff members and alert them, via their tags, to handle the event and move or accompany the respective restricted object back to the safe area. Fixed tag 968D and fixed tag 968E are positioned at the passages between the buffer area and the lock area for detecting entry of a restricted object into the lock area. Optionally, additional fixed tags 962L may be scattered within the lock area to detected restricted objects with the lock area. Possibly, in some embodiments, fixed tag 968D and fixed tag 968E, as well as fixed tags 962L, are preferably also configured to autonomously send a locking signal to the elevator 204 and door of staircase 906. It will be appreciated that the concept of locking an elevator may be actually implemented by preventing the elevator door from closing, or by disabling the elevator altogether through the elevator's controller (not shown). Fixed tag 968F and fixed tag 968G are positioned at the exits, i.e. the passages between the lock area and the alarm area, for detecting entry of a restricted object into the alarm area, i.e. within the elevator or staircase. Possibly, in some implementations, fixed tag 968F and fixed tag 968G are also configured to autonomously trigger an audible alarm and initiate an alarm event procedure such as calling for intervention by security personnel. It will be appreciated that fixed tags 968B-968G, 962B and 962L in the exemplary embodiment of FIG. 10A, are beacon detectors fixed at a selected points, such as on a ceiling or a wall, for detecting object beacons in their proximity. Their design is similar to tag 110 of FIG. 1A, modified for continuous operation in a fixed location, which preferably implies continuous network connection and drawing energy from the site's electrical network.

Figure 10B:
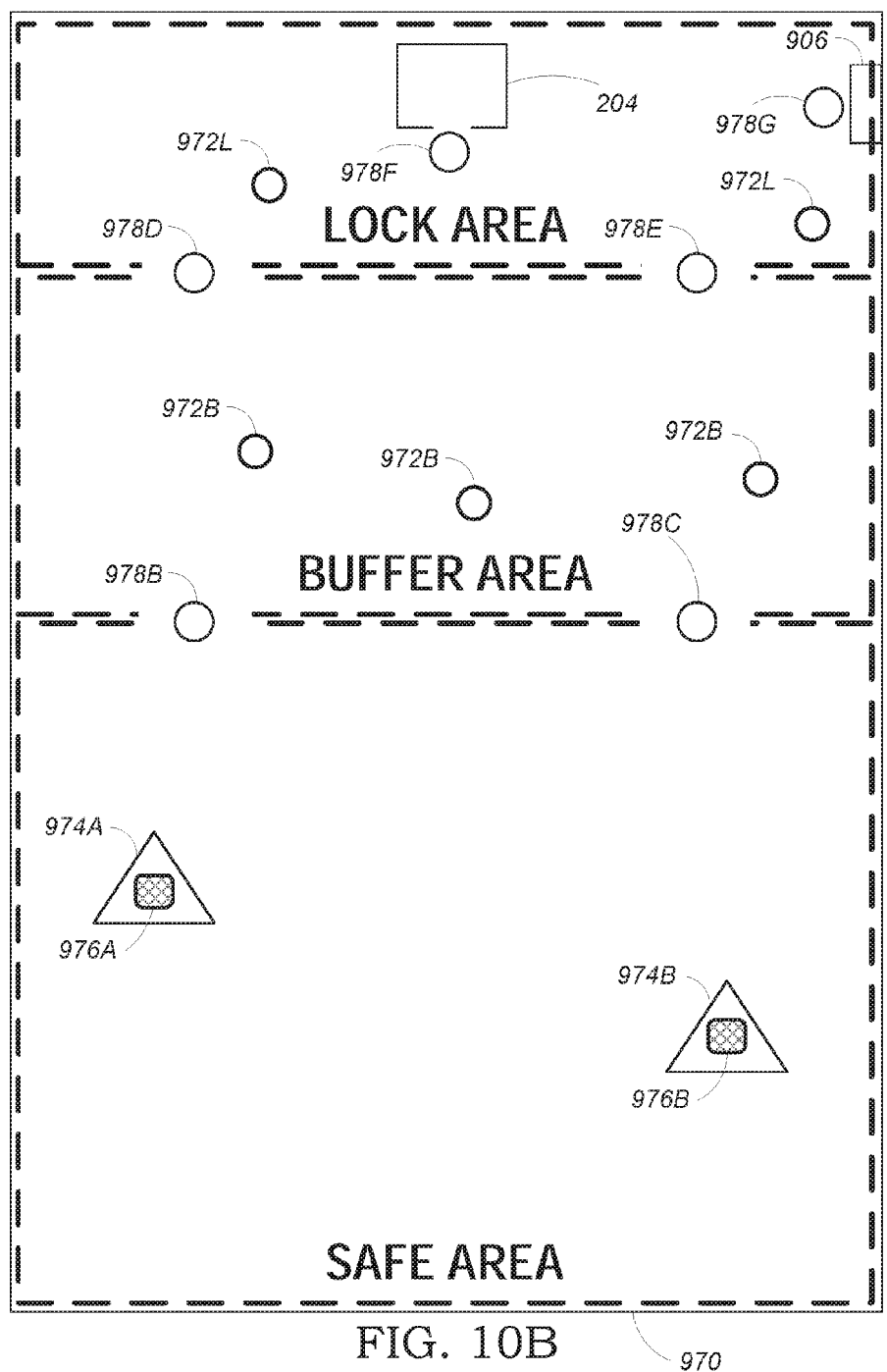

FIG. 10B depicts an embodiment of a confined area 970 that is similar to the embodiment of FIG. 10A, except for swapping the roles of tags and beacons. Thus, in confined area 970, restricted object 974A and restricted object 974B bear smart object tag 976A and smart object tag 976B, respectively. Border beacon 978B and border beacon 978C cooperate with the smart object tags to detect, by the tags, crossing the border between the safe area and the buffer area; border beacon 978D and border beacon 978E cooperate with the smart object tags to detect, by the tags, their crossing the border between the buffer area and the lock area; and border beacon 978F and border beacon 978G cooperate with the smart object tags to detect, by the tags, their crossing the border between the lock area and the alarm area. Location beacons 972B and 972L are optionally added for the detection of restricted objects, by their tags, within the buffer area and lock area, respectively. It is the smart object tags that either report border crossings or unauthorized location to a control, or are configured to autonomously trigger a staff, lock or alarm action respective to the detected border crossing, as depicted with reference to FIG. 10A above.

Figure 10C:
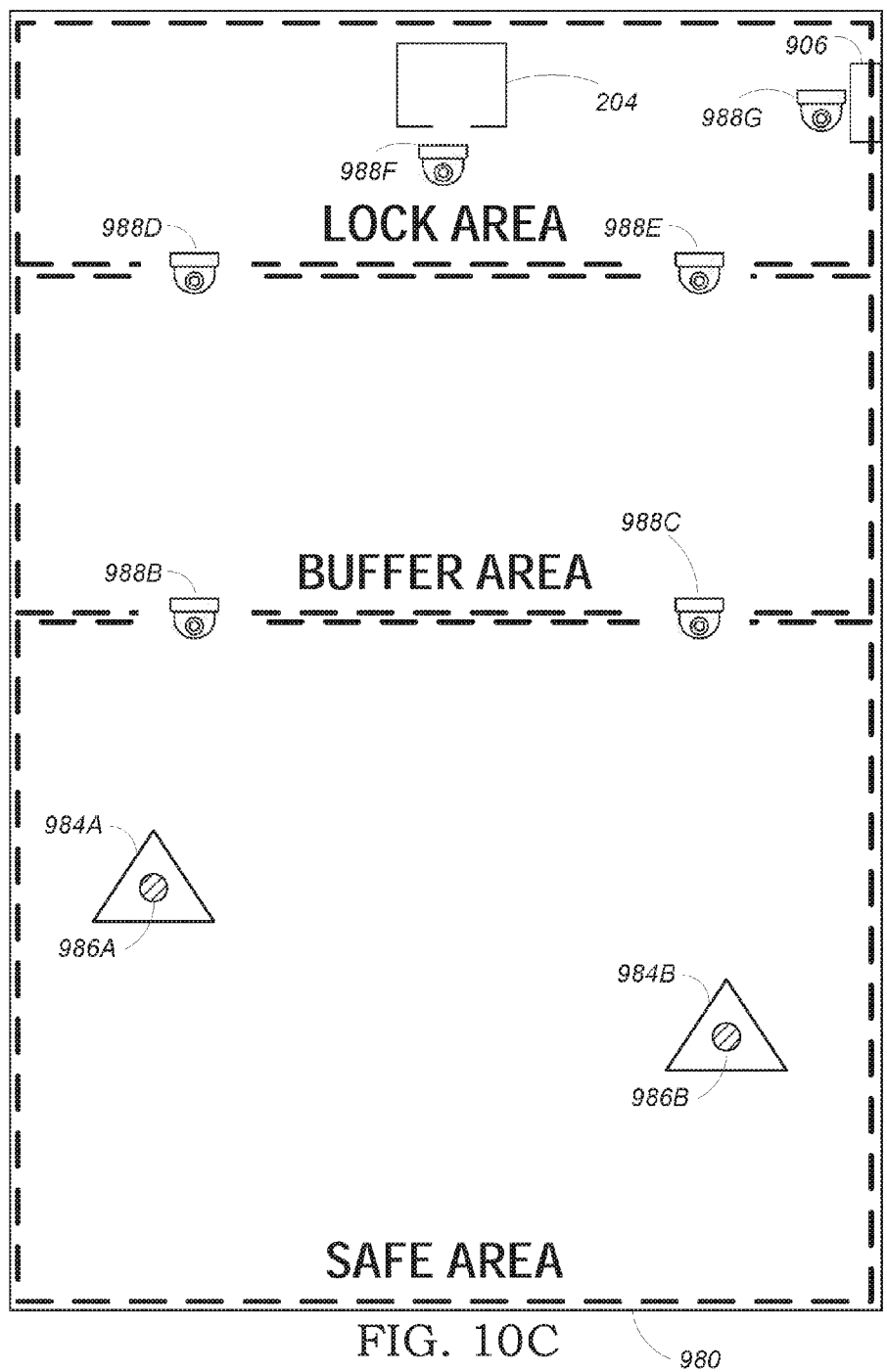

FIG. 10C describes a scenario of a confined area 980 that is similar to the scenario of FIG. 10A, except that fixed tags 968B-968G are replaced by cameras 988B-988G, respectively; while object beacons 966A-966B are replaced by visual features 986A-986B, respectively. Visual features 986A-986B may identify restricted objects either individually, for example by including a machine-readable identifier, such as a machine-recognizable text, QR code or bar code, or identify group of restricted objects, such as restricted residents or restricted assets, for example by a distinctive color of a label or a dress. When any of cameras 988B-988G detects any of visual features 986A-986B crossing a border between zones, a respective processor, such as the processor of a fixed tag that includes the camera or of a control reported by the camera, may actuate an action such as calling for staff intervention, locking exits or triggering an alarm, as depicted above with reference to FIG. 10A. In some embodiments, for security and/or restricted resident dignity, visual features my be marked in the invisible spectrum, for example in the infrared spectrum, with the cameras using appropriate filters to recognize such visual features. It will be appreciated that additional cameras may be fixed and operate within the buffer area and the lock area similarly to tags 962B and tags 962L of FIG. 10A.

It will be noted that by using fixed tags that include cameras, the scenarios of confined area 960 and confined area 980 may be combined, so that some restricted objects my be detected and identified by their object beacons, while other restricted objects my be detected and identified by their visual features. It will be also noted that that architectures of FIGS. 10A-10C may be combined and mixed, for example by restricted residents bearing tags while restricted assets having beacons attached to them.

It will also be noted that in the embodiments of FIGS. 10A-10C, a tag or a camera cooperates with a beacon or a visual feature to recognize that an asset is moving from one area to another or is already in the buffer or lock area. There are two further steps that may be performed, according to the system architecture, by either the tag or by a control (such as control 174 of FIGS. 1A-1B) to which the tag or camera is reporting: (a) deciding whether the detected moving of the respective restricted object is authorized or not; and (b) triggering an action, such as: selecting and calling staff members to intervene; locking exists; or actuating an alarm.

Figure 11A:
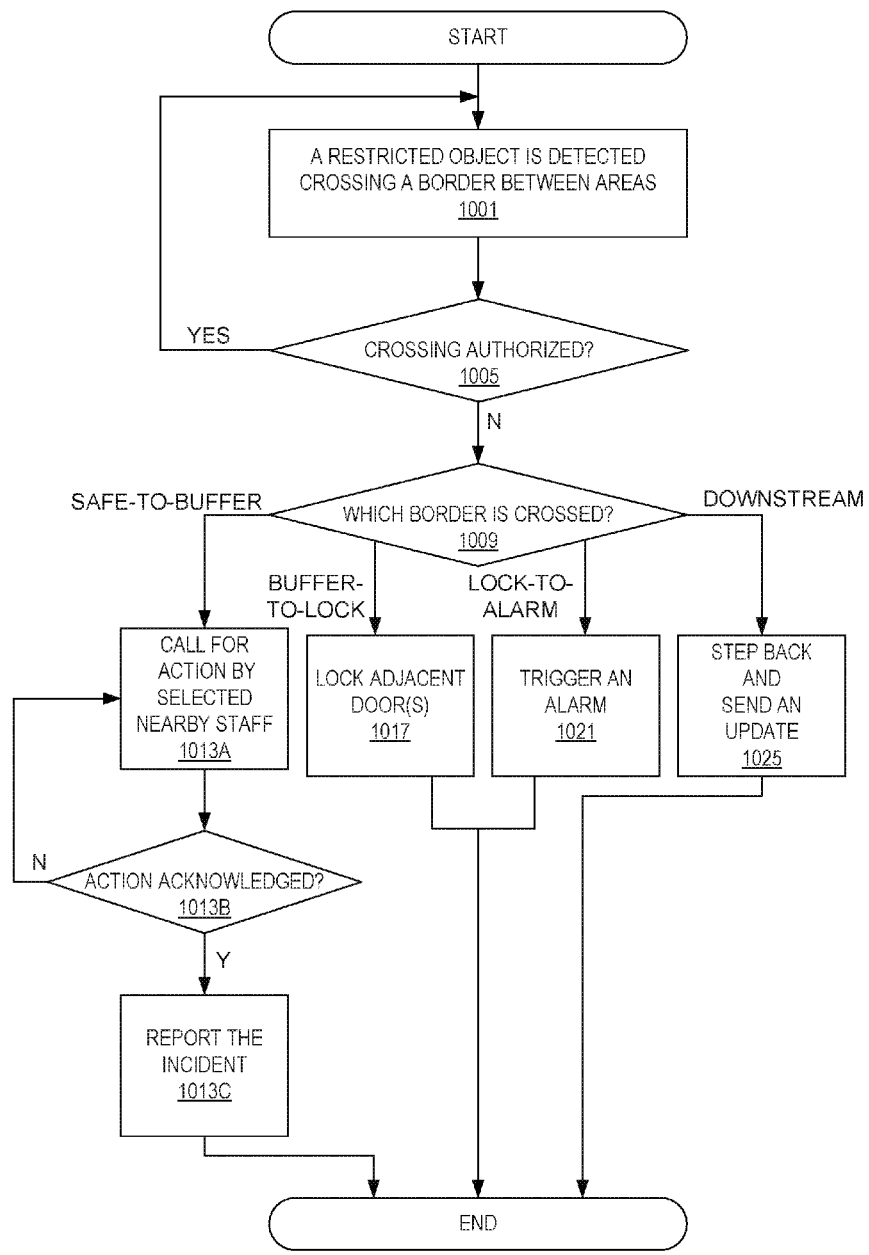
FIGS. 11A, 11B and 12 are flowcharts describing the process of operating a multi-level border control system.

FIG. 11A depicts the operation of the multi-level border security arrangement described with reference to FIGS. 10A-10C above. In step 1001, a restricted object, such as a person or an asset, is detected crossing a border between areas. Such detection is made via a tag detecting a beacon under the arrangement of either FIG. 10A or the arrangement of FIG. 10B, or by a camera detecting a visual feature under the arrangement of FIG. 10C. Step 1005 decides whether the border crossing is authorized or not. If the border crossing is authorized, by either a permit received via communication from a supervisor, or by verifying, via a personal tag or beacon of a person that maintains close proximity to the restricted object, that the restricted object is accompanies by a person authorized to move the restricted object, then step 1005 loops back to wait for another border crossing detection. If step 1005 concludes that the border crossing is not authorized, then step 1009 decides, according to the type of border crossed, what action to take. If the detected crossing is from the safe to the buffer area, then step 1013A triggers a notification to the tag or tags of one or more selected staff members in the vicinity of the crossing point, to rush and accompany the crossing restricted object back to the safe area. In the action is picked and acknowledged in steps 1013B by one of the notified staff members, then in step 1013C the incident is reported; if step 1013B does not receive acknowledgement within a short period, then the process loops back to step 1013A to call for action of additional staff members. If the crossing is found by step 1009 to be from the buffer to the lock area, then step 1017 triggers locking or disabling the respective exist(s), such as the elevator and the staircase door. If the crossing is found by step 1009 to be from the lock area to the alarm area, then step 1021 triggers an alarm. If the crossing is found by step 1009 to be downstream, i.e. from the alarm to the lock area, from the lock area to the buffer area, or from the buffer area to the safe area, then step 1025 triggers a step-back procedure, such as turning an alarm off or unlocking exits, and an update describing the crossing event is sent to the involved staff members.

Figure 11B:
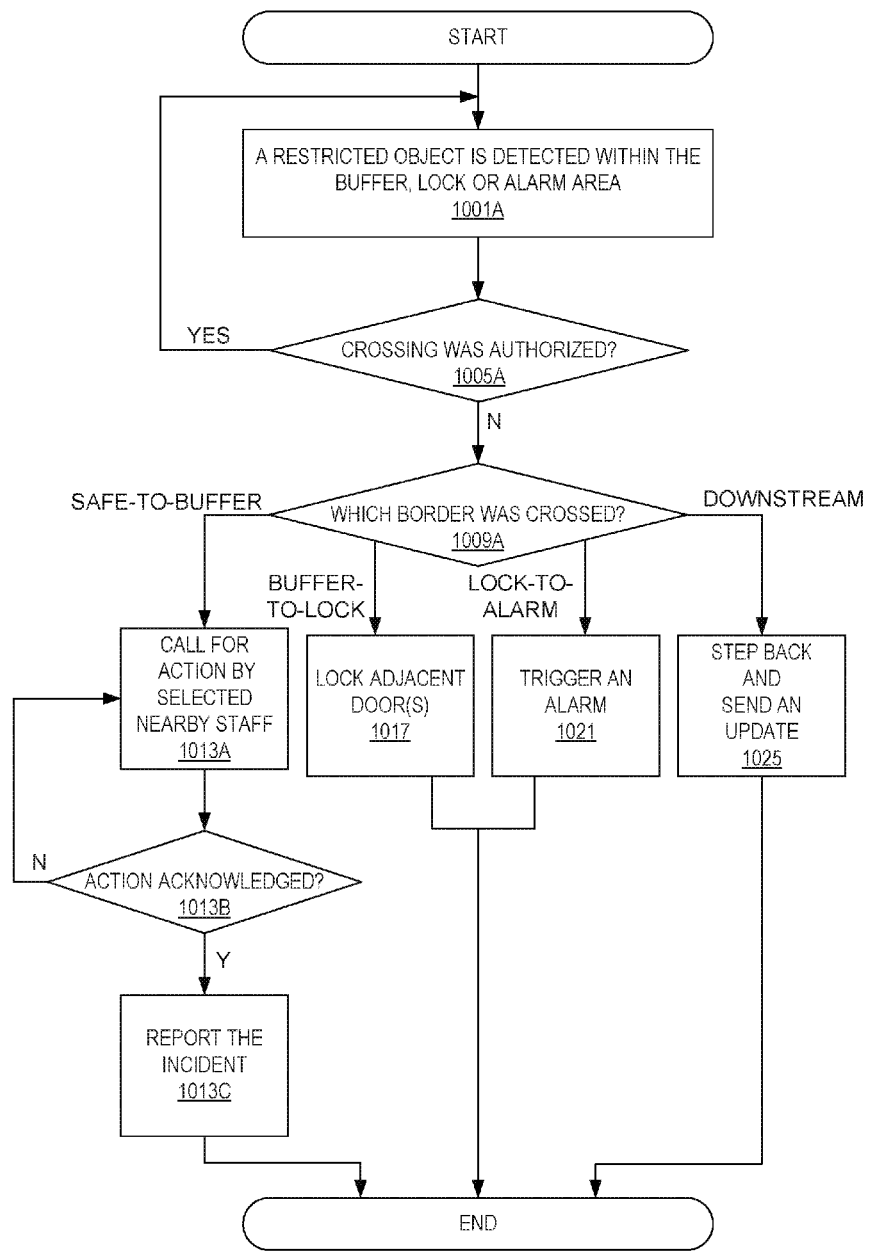

FIG. 11B is similar to FIG. 11A, except that a restricted object is first detected in step 1001A within the buffer area, lock area or alarm area, instead of at the respective border; for example, when the detection is made by fixed tags 962B or fixed tags 962L within the respective area (FIG. 10A), rather than at the respective borders by fixed tags 968B-968E. Step 1005A compares the current location to the last known location to interpret that current location as a border crossing event, and checks whether the crossing was authorized. If crossing is found not authorized, then step 1009A diverts to actions according to the nature of the crossed border, as depicted in FIG. 11A above.

Figure 12:
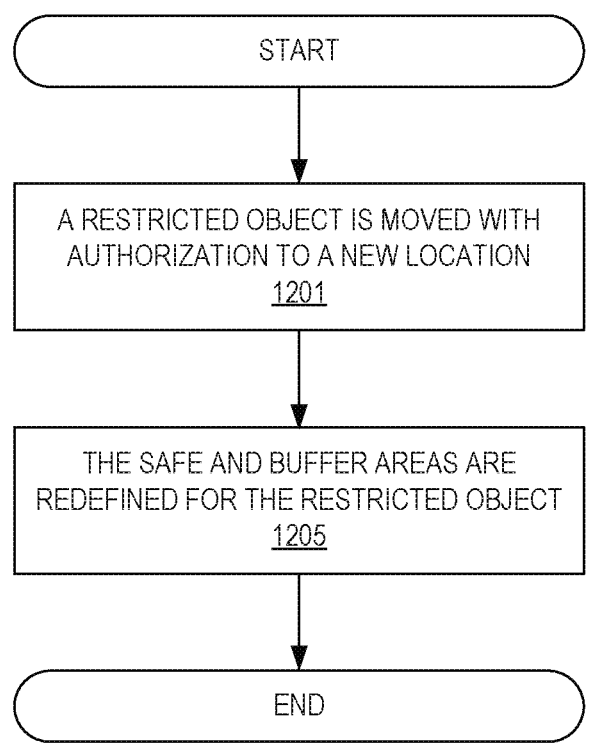

FIG. 12 is a flowchart that describes an authorized relocation process of a restricted object. In step 1201 a restricted object is moved to a new location according to the process of FIG. 11 or FIG. 11A. Since all border crossings are authorized, all border crossings are performed without step 1005/1005A triggering any of the actions that follow step 1009/1009A. When reaching the intended location, then step 1205 resets the definitions of the safe area and buffer area of the moved object according to the new current location. For example, in a healthcare facility, a restricted resident is escorted by a staff member to a large dining room for lunch and is left by himself at the dining room, that resident's safe area may be redefined to encompass the dining room, and leaving the dining room without escorting by an authorized person will then trigger step 1013A of FIG. 11/11A. Such relocation and redefinition of the safe and buffer areas may be recorded centrally, in a system that tracks objects and/or personalizes safe areas per restricted object, or just be established de-facto, by the very presence of a restricted object in a new area that is generally defined as a safe area.

It will be reemphasized that the steps of FIGS. 11A, 11B and 12 may be performed, according to selected system architectures, individually or cooperatively, by processors of a staff tag, a resident tag, an asset tag, a fixed tag or a control. Accordingly, the expression "at least one processor" that perform part or all of the steps of the process of FIG. 11/11A may relate to performing steps by any one or combination of processors included in participating tags, controls and/or servers.

Non-Healthcare Applications

For clarity and consistency, the exemplary embodiments depicted above related primarily to healthcare facilities. It will be appreciated, however, that the teachings of the present disclosure may selectively pertain a to variety of institutional sites, such as manufacturing plants, educational institutions, government buildings, office building, ships, etc., that can benefit from zone-level locating of objects or multi-level border control.

Self Learning, Calibration and Improvement

The systems and methods depicted above are expected to produce tangible and measurable results in locating and securing assets, in effectively directing staff members toward selected assets, and in border control within sites. Exceptions are easily noticed: an asset whose location remains unknown for a prolonged duration; misdirecting a staff member toward an asset; or a staff member spending excessive time in screening a zone for finding an asset.

Exceptions may be automatically detected at location data stores and controls (FIG. 1B), and/or manually reported by staff members. Such exceptions may motivate and guide redefining zones, better placing location beacons, adding beacon detectors, changing the sensitivity threshold of tag receivers, upgrading the network communication, or revising the criteria for deciding between conflicting locating reports.

Improvement can be also made by educating and training staff members with regard to where to move assets that completed a task, for example into preassigned asset parking areas; how to report the location of an unused asset; or who is authorized to move a certain asset. Visitors may also be educated, via signs and brochures, to request staff assistance for moving an unused asset and never move an asset by themselves.

The above measures may substantially improve the performance of locating and securing assets with minimal additional investment in hardware and installation.

CONCLUSION

The systems and methods taught by the present disclosure provide a compact locating and directing system for assets and people, that can be afforded by and adequately serve many sites that cannot or will not afford conventional RTLS, access control or security systems.

While the invention has been described with respect to a limited number of embodiments, it will be appreciated by persons skilled in the art that the present invention is not limited by what has been particularly shown and described herein. Rather the scope of the present invention includes both combinations and sub-combinations of the various features described herein, as well as variations and modifications which would occur to persons skilled in the art upon reading the specification and which are not in the prior art.

What is claimed is:

1. A system for keeping a restricted object within a confined area that forms part of an institutional site, the confined area having: (i) one or more lockable exits which can be remotely locked to prevent exit of the restricted object from said confined area, (ii) a safe area where the restricted object is designated to stay, (iii) a buffer area adjacent to the safe area, and (iv) a lock area situated between the buffer area and the one or more lockable exits, the system comprising:

at least one beacon, each beacon of the at least one beacon includes a wireless transmitter configured to recurrently transmit a short-range wireless signal; and at least one tag, each tag of the at least one tag being a device that is either a personal tag borne by a person, an asset tag attached to an asset, or a fixed tag that is fixed at a location that is either at the border of or within the buffer area or lock area, each tag of the at least one tag including:
- a receiver configured to receive short-range wireless signals transmitted from the at least one beacon,
- a network communication device configured to at least wirelessly communicate with other tags, and
- a processor programmed to:
  - based on a short-range wireless signal sent from the at least one beacon and received via the receiver, identify whether the restricted object is in the buffer area or in the lock area,
  - check whether the restricted object is authorized to leave the safe area,
  - upon recognizing that the restricted object is in the buffer area and is not authorized to leave the safe area, send a message to a tag of a selected staff member, the message instructing to move the restricted object back to the safe area prior to the restricted object reaching the lock area, and
  - upon recognizing that the restricted object is in the lock area and is not authorized to leave the safe area, send a locking signal to at least one lockable exit of the one or more lockable exits to prevent exit of the restricted object from said confined area.

2. The system of claim 1, wherein the at least one processor is further programmed to:
- identify one or more staff members that are currently in vicinity of the restricted object; and
- select the selected staff member from the one or more staff members that are currently in vicinity of the restricted object.

3. The system of claim 1, wherein the at least one tag is further programmed to:
- wait for acknowledgement from a tag of a staff member of the at least one staff member; and
- if no acknowledgement is received within a predefined period of time: send a message to a tag of another selected staff member within the institutional site.

4. The system of claim 1, wherein either:
(1) the at least one beacon includes multiple different beacons that are fixed at locations within the institutional site, and the at least one tag is a tag attached to the restricted object; or
(2) the at least one beacon is a beacon attached to the restricted object, and the at least one tag includes multiple tags that are fixed at locations within the institutional site.

5. The system of claim 1, wherein the check is made by verifying that the restricted object is escorted by a person authorized to move the restricted object.

6. A system for keeping a movable restricted object within a confined area that forms part of an institutional site, the confined area having: (i) one or more lockable exits which can be remotely locked to prevent exit of the restricted object from said confined area, (ii) a safe area where the restricted object is designated to stay, (iii) a buffer area adjacent to the first area, and (iv) a lock area situated between the buffer area and the one or more lockable exits, the system comprising:

an object identifier, that is a beacon or a visual feature, borne by the restricted object;

a first fixed tag that is a device fixed either at the border of or within the buffer area and operative to:
- communicate with the object identifier to detect whether the restricted object is in the buffer area,
- check whether the restricted object is authorized to leave the safe area, and
- upon recognizing that the restricted object is in the buffer area and is not authorized to leave the safe area: send a message to a tag of a selected staff member, the message instructing the selected staff member to move the restricted object back to the safe area prior to the restricted object reaching the lock area; and a second fixed tag that is a device fixed either at the border of or within the lock area and operative to:
- communicate with the object identifier to detect whether the restricted object is in the lock area,
- check whether the restricted object is authorized to leave the safe area, and
- upon recognizing that the restricted object is in the lock area and is not authorized to leave the first area: send a locking signal to at least one lockable exit of the one or more lockable exits to prevent exit of the restricted object from said confined area within said institutional site.

7. The system of claim 6, wherein the first fixed tag is further operative to:
select the selected staff member from one or more staff members that are currently in vicinity of the restricted object.

8. The system of claim 6, wherein the first fixed tag is further operative to:
- wait for acknowledgement from a tag of the selected staff member; and
- if no acknowledgement is received within a predefined period of time: send a message to a tag of another staff member within said institutional site.

9. The system of claim 6, wherein the restricted object is one of: a restricted resident of a healthcare facility, or a restricted asset.

10. The system of claim 6, wherein the check is made by the first fixed tag or by the second fixed tag by verifying that the restricted object is escorted by a person authorized to move the restricted object.

11. A system for keeping a movable restricted object within a fixed confined area that forms part of an institutional site, the confined area having: (i) one or more lockable exits that are remotely lockable to prevent exit of the restricted object from said confined area, (ii) a safe area where the restricted object is designated to stay, (iii) a buffer area adjacent to the first area, and (iv) a lock area situated between the buffer area and the one or more lockable exits, the system comprising:

a first beacon fixed at the border of or within the buffer area and configured to recurrently transmit a short-range wireless signal;

a second beacon fixed at the border of or within the lock area and configured to recurrently transmit a short-range wireless signal; and a tag that is a device attached to the restricted object and operative to:
- communicate with the first fixed beacon to detect whether the restricted object is in the buffer area,
- communicate with the second fixed beacon to detect whether the restricted object is in the lock area, check whether the restricted object is authorized to leave the safe area, upon recognizing that the restricted object is in the buffer area and is not authorized to leave the safe area: autonomously send a message to a tag of a selected staff member within said institutional site, the message instructing the selected staff member to move the restricted object back to the safe area prior to the restricted object reaching the lock area, and upon recognizing that the restricted object is in the lock area and is not authorized to leave the safe area: send a locking signal to at least one lockable exit of the one or more lockable exits to prevent exit of the restricted object from said confined area.

12. The system of claim 11, wherein the tag is further operative to:

detect one or more staff members that are currently in vicinity of the restricted object; and select the selected staff member from the one or more staff members that are currently in vicinity of the restricted object.

13. The system of claim 11, wherein the tag is further operative to:

wait for acknowledgement from a tag of the selected staff member; and if no acknowledgement is received within a predefined period of time: send a message to a tag of another staff member.

14. The system of claim 11, wherein the restricted object is one of: a restricted resident of a healthcare facility, or a restricted asset.

15. The system of claim 11, wherein the check is made by the tag by verifying that the restricted object is escorted by a person authorized to move the restricted object.

16. A method of operation of at least one tag and at least one beacon for keeping a restricted object within a confined area that forms part of an institutional site, the confined area having one or more lockable exits which can be remotely locked to prevent exit of the restricted object from said confined area, the confined area including:

a safe area where the restricted object is designated to stay, a buffer area adjacent to the first area, and a lock area situated between the buffer area and the one or more lockable exit, each of the at least one tag being a device that is either a personal tag borne by a person, an asset tag attached to an asset, or a fixed tag that is fixed at a location that is either at the border of or within the buffer area or lock area, each tag of the at least one tag; the method comprising:

recurrently transmitting, via a wireless transmitter of each beacon of the at least one beacon, a short-range wireless signal;

receiving, via a short-range wireless receiver of each tag of the at least one tag, the short-range wireless signal;

wirelessly communicating, via a network communication device of each tag of the at least one tag, with other tags;

based on the received short-range wireless signal, detecting, by the at least one tag, whether the restricted object is in the buffer area or in the safe area;

checking, by the at least one tag, whether the restricted object is authorized to leave the safe area;

upon recognizing that the restricted object is in the buffer area and is not authorized to leave the safe area: sending, by the at least one tag, a message to a tag of a selected staff member, the message instructing the selected staff member to move the restricted object back to the safe area prior to the restricted object reaching the lock area; and upon recognizing that the restricted object is in the lock area and is not authorized to leave the safe area: sending, by the at least one tag, a locking signal to at least one lockable exit of the one or more lockable exits to prevent exit of the restricted object from said confined area within said institutional site.

17. The method of claim 16, further comprising, prior to the sending a message to the tag of the selected staff member: selecting, by the at least one tag, the selected staff member from one or more staff members that are currently in vicinity of the restricted object.

18. The method of claim 16, further comprising:

waiting for acknowledgement from the selected staff member; and if no acknowledgement is received within a predefined period of time: sending a message to a tag of another staff member.

19. The method of claim 16, wherein the restricted object is one of: a restricted resident of a healthcare facility, or a restricted asset.

20. The method of claim 16, wherein the checking is made by verifying that the restricted object is escorted by a person authorized to move the restricted object.

* * * * *